(12) United States Patent
Felsovalyi et al.

(10) Patent No.: US 11,724,038 B2
(45) Date of Patent: Aug. 15, 2023

(54) SYRINGE ASSEMBLY WITH INVERSE DELIVERY

(71) Applicant: Becton Dickinson France, Le Pont-de-Claix (FR)

(72) Inventors: Flora Felsovalyi, Bloomingdale, NJ (US); Eric Schiller, Kinnelon, NJ (US); Michael Quinn, East Hanover, NJ (US)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 17/961,319

(22) Filed: Oct. 6, 2022

(65) Prior Publication Data

US 2023/0029689 A1 Feb. 2, 2023

Related U.S. Application Data

(63) Continuation of application No. 16/688,489, filed on Nov. 19, 2019, now Pat. No. 11,491,279, which is a continuation of application No. 15/140,886, filed on Apr. 28, 2016, now Pat. No. 10,507,288, which is a continuation of application No. 12/859,569, filed on Aug. 19, 2010, now Pat. No. 9,352,096.

(60) Provisional application No. 61/235,805, filed on Aug. 21, 2009.

(51) Int. Cl.
*A61M 5/315* (2006.01)
*A61M 5/31* (2006.01)
*A61M 5/19* (2006.01)

(52) U.S. Cl.
CPC .......... *A61M 5/31511* (2013.01); *A61M 5/19* (2013.01); *A61M 5/3134* (2013.01); *A61M 5/3135* (2013.01); *A61M 5/3137* (2013.01); *A61M 5/3148* (2013.01); *A61M 5/31515* (2013.01); *A61M 2005/3121* (2013.01); *A61M 2005/3123* (2013.01); *A61M 2005/3139* (2013.01); *A61M 2005/31516* (2013.01); *A61M 2005/31518* (2013.01)

(58) Field of Classification Search
CPC .. A61M 2005/3123; A61M 2005/3139; A61M 2005/31518; A61M 5/19; A61M 5/3134; A61M 5/3135; A61M 5/3137; A61M 5/3148; A61M 5/315; A61M 5/31511; A61M 5/31515
See application file for complete search history.

(56) References Cited

U.S. PATENT DOCUMENTS

| | | | |
|---|---|---|---|
| 1,074,965 | A | 10/1913 | McClellan |
| 1,231,772 | A | 7/1917 | Meyer |
| 1,624,990 | A | 4/1927 | Smith |
| 1,670,570 | A | 5/1928 | Hein |

(Continued)

FOREIGN PATENT DOCUMENTS

| | | |
|---|---|---|
| EP | 1520597 A1 | 4/2005 |
| GB | 2418616 A | 4/2006 |
| WO | 0035518 A | 6/2000 |

*Primary Examiner* — Shefali D Patel
(74) *Attorney, Agent, or Firm* — The Webb Law Firm

(57) ABSTRACT

A reduced profile syringe assembly is provided that includes an overall profile that is substantially similar to a profile of a syringe barrel. The syringe assembly includes a plunger rod that is significantly disposed within the syringe barrel when filled for use, with the plunger rod adapted to be retracted from the syringe barrel during dispensing of contents of the syringe barrel.

4 Claims, 17 Drawing Sheets

(56) References Cited

U.S. PATENT DOCUMENTS

| | | |
|---|---|---|
| 2,062,285 A | 12/1936 | Bergman |
| 3,957,051 A | 5/1976 | Topham |
| 4,287,819 A | 9/1981 | Emerit |
| 4,498,904 A | 2/1985 | Turner et al. |
| 4,639,248 A | 1/1987 | Schweblin |
| 4,813,937 A * | 3/1989 | Vaillancourt ......... A61M 5/165 604/230 |
| 4,834,714 A | 5/1989 | Lascar |
| 5,104,380 A | 4/1992 | Holman et al. |
| 5,562,635 A | 10/1996 | Whisson |
| 5,697,915 A | 12/1997 | Lynn |
| 5,743,886 A | 4/1998 | Lynn et al. |
| 5,759,177 A | 6/1998 | Whisson |
| 5,762,633 A | 6/1998 | Whisson |
| 5,769,825 A | 6/1998 | Lynn |
| 6,231,550 B1 | 5/2001 | Laughlin |
| 6,290,678 B1 | 9/2001 | Aydelotte et al. |
| 6,368,308 B1 | 4/2002 | Nerney |
| 6,554,792 B2 | 4/2003 | Hughes |
| 6,692,468 B1 | 2/2004 | Waldenburg |
| 6,746,420 B1 * | 6/2004 | Prestidge .......... A61M 25/0631 604/164.08 |
| 6,830,564 B2 | 12/2004 | Gray |
| 7,077,826 B1 | 7/2006 | Gray |
| 7,118,556 B2 | 10/2006 | Nerney |
| 7,175,609 B1 | 2/2007 | Gray |
| 2001/0021820 A1 | 9/2001 | Lynn |
| 2003/0040701 A1 | 2/2003 | Dalmose |
| 2005/0119610 A1 | 6/2005 | Peuker et al. |
| 2006/0264824 A1 | 11/2006 | Swisher, III |
| 2007/0088285 A1 | 4/2007 | Sharp et al. |
| 2008/0114306 A1 | 5/2008 | Bare |

* cited by examiner

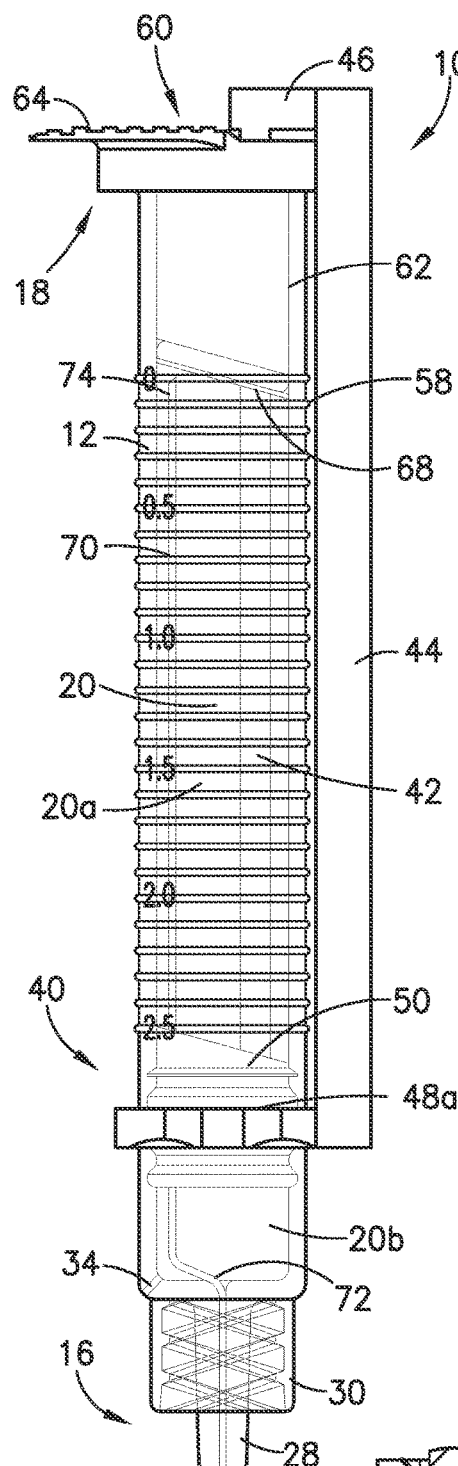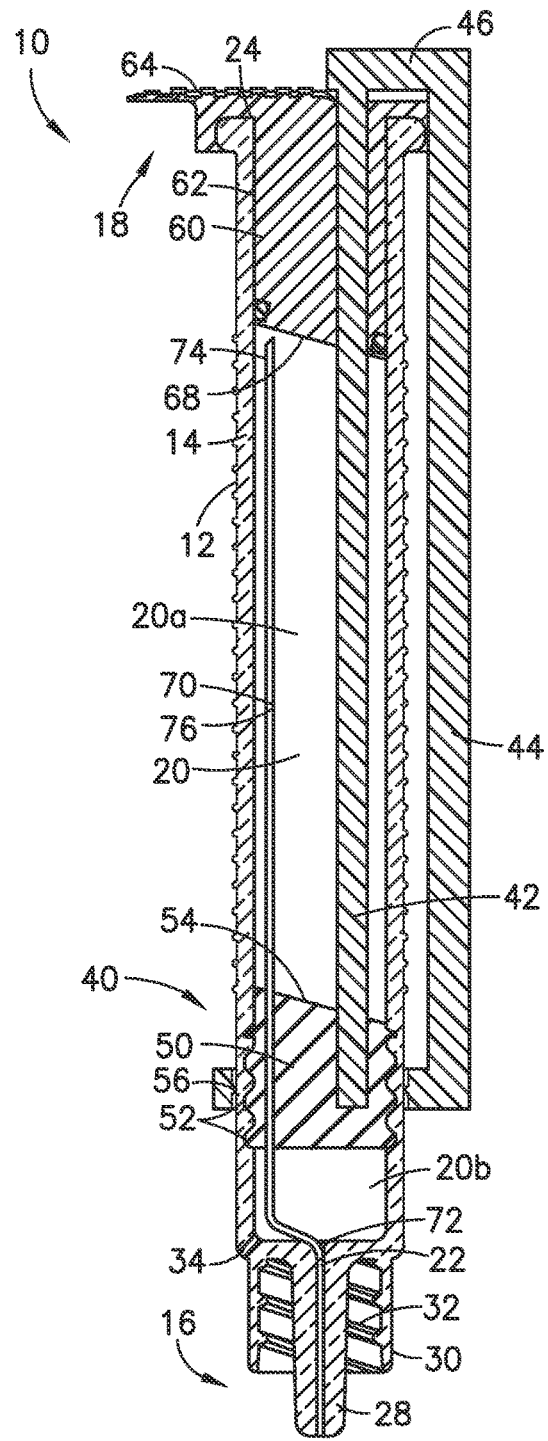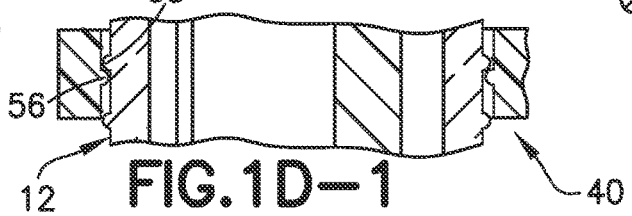

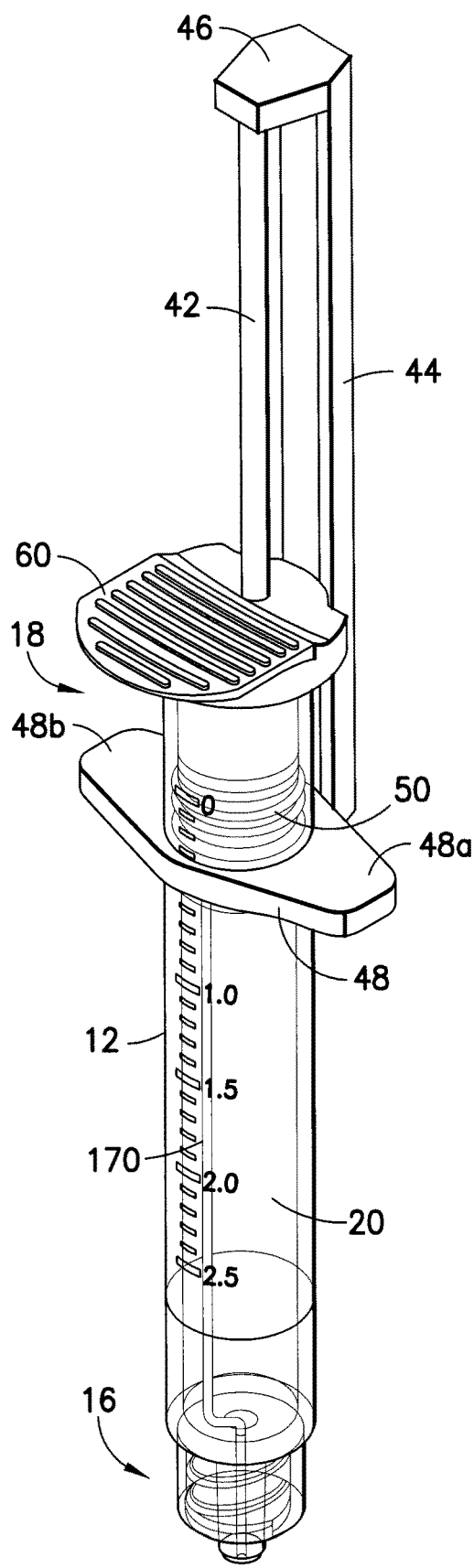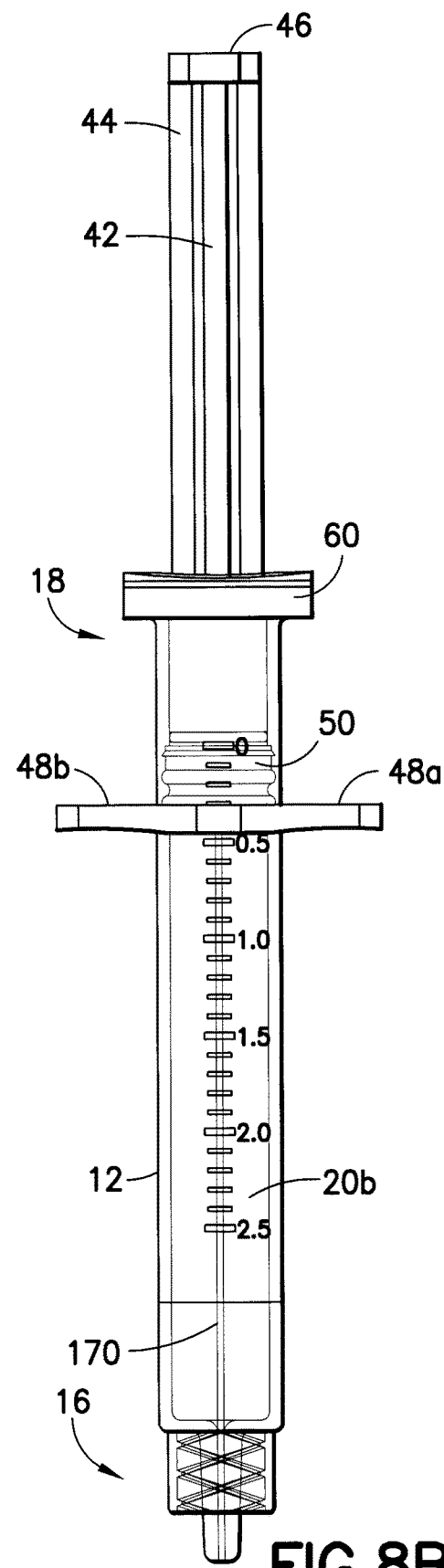

SYRINGE ASSEMBLY WITH INVERSE DELIVERY

CROSS REFERENCE TO RELATED APPLICATION

This application is a continuation of U.S. patent application Ser. No. 16/688,489 entitled "Syringe Assembly with Inverse Delivery", filed Nov. 19, 2019, which is a continuation application of U.S. patent application Ser. No. 15/140,886 entitled "Syringe Assembly with Inverse Delivery", filed Apr. 28, 2016 (now U.S. Pat. No. 10,507,288), which is a continuation application of U.S. patent application Ser. No. 12/859,569 entitled "Syringe Assembly with Inverse Delivery", filed Aug. 19, 2010 (now U.S. Pat. No. 9,352,096), which claims priority to U.S. Provisional Application No. 61/235,805 entitled "Syringe Assembly with Inverse Delivery", filed Aug. 21, 2009, the entire disclosures of each of which are hereby incorporated herein by reference.

BACKGROUND OF THE INVENTION

Field of the Invention

The present invention is directed to a syringe assembly adapted for dispensing and delivery of a fluid. More particularly, the present invention is directed to a syringe assembly such as a hypodermic syringe having a reduced profile prior to use, and which is adapted for delivering the contents thereof through a conventional movement by the user, but involving an inverse delivery operation.

Related Technology

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel, and with a finger flange at the other end of the plunger rod extending out of the barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Packaging of such pre-filled syringes, however, tends to be bulky. A pre-filled syringe is typically packaged with the opening at the front end of the barrel including a cap thereover and with the plunger rod retracted out of the back end of the syringe barrel, with the fluid pre-filled within the syringe barrel. Such packaging creates an elongated package that can be awkward for shipping and storage.

Pre-filled syringes are often filled with narcotics or other drugs at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packing footprint, to reduce the storage space required for containing the syringe. It is also desirable to produce syringes that are uniform in terms of an outer surface shape to allow for stacking of these syringes within the storage cabinet.

SUMMARY OF THE INVENTION

The present invention provides a syringe assembly having a reduced profile prior to use, thereby occupying less space than a conventional syringe and providing a mechanism for reduced overall size and for efficient packaging that reduces or eliminates excess waste. Further, actuation of a syringe assembly of the present invention is accomplished using a similar operation as with a conventional syringe, thereby providing a standardized mechanism for ease of use.

In one embodiment of the present invention, the reduced profile is achieved by providing a syringe assembly that, when filled, comprises an overall profile that is substantially similar to the profile of the syringe barrel. This may be accomplished by providing the syringe assembly with a plunger rod that is significantly disposed within the syringe barrel when filled for use, with the plunger rod adapted to be retracted from the syringe barrel during dispensing of the contents of the syringe barrel.

One embodiment contemplates a syringe assembly including a syringe barrel having an inside surface defining a chamber, an open proximal or rearward end, and a distal or forward end having an opening therethrough. A plunger assembly is disposed at least partially within the syringe barrel, with the plunger assembly comprising an elongated plunger rod and a plunger head disposed on the plunger rod and slidably disposed within the syringe barrel. The plunger head separates the chamber of the syringe barrel into a proximal chamber adjacent the proximal end and a distal chamber adjacent the distal end. A conduit extends between the proximal chamber and the opening at the distal end of the syringe barrel. The syringe assembly is adapted to contain a fluid in the proximal chamber, such fluid being expelled through the conduit and out of the opening at the distal end of the syringe barrel upon movement of the plunger head toward the proximal end of the syringe barrel. Movement of the plunger head toward the proximal end of the syringe barrel occurs based on conventional operation of expelling fluid from a conventional syringe with a squeezing movement between a thumb and forefinger. Such movement is well recognized to syringe users, which typically involves squeezing between a thumb pad on a plunger rod and a forefinger on a finger flange on a syringe barrel. Through embodiments of the present invention, an inverse delivery is accomplished with similar operational movement of a conventional syringe, thereby achieving a reduced profile syringe without any perceived change in operational use by the user.

In certain embodiments, the plunger assembly may further include an actuator portion at least partially extending externally outside of the syringe barrel and adapted to effect movement of the plunger head within the syringe barrel. The actuator portion may be interconnected to the plunger head, for example, through the sidewall of the syringe barrel or through an open proximal end of the syringe barrel. The actuator portion may include at least one flange configured to receive a forefinger of a user, while the proximal end of the syringe barrel may be closed with a closure that may include a thumb pad. Such flange and thumb pad are adapted to accommodate the conventional squeezing operational movement of a conventional syringe while accomplishing the inverse delivery of the contents of the syringe.

In another embodiment, a syringe assembly is provided including a syringe barrel having an inside surface defining a chamber, a proximal end, and a distal end having an opening therethrough. A plunger assembly including a plunger head is slidably disposed within the syringe barrel, with the plunger head separating the chamber of the syringe barrel into a proximal chamber adjacent the proximal end and a distal chamber adjacent the distal end. The syringe assembly further includes a thumb pad portion adjacent the proximal end of the syringe barrel for accommodating a thumb of a user, and at least one finger flange extending externally of the syringe barrel for accommodating at least one forefinger of a user, with the finger flange adapted to effect movement of the plunger head within the syringe barrel. Squeezing movement between a user's thumb on the thumb pad portion and a user's forefinger on the finger flange effects movement of the plunger head toward the proximal end of the syringe barrel. In this manner, inverse delivery of the syringe contents is accomplished with similar operational movement of a conventional syringe, thereby achieving a reduced profile syringe without any perceived change in operational use by the user.

In yet a further embodiment, a pre-filled syringe assembly is provided including a syringe barrel having an inside surface defining a chamber, a proximal end, and a distal end having an opening therethrough. The assembly further includes a plunger assembly comprising an elongate plunger rod substantially disposed within the syringe barrel and a plunger head disposed on the plunger rod and slidably disposed within the syringe barrel. The plunger head separates the chamber of the syringe barrel into a proximal chamber adjacent the proximal end and a distal chamber adjacent the distal end. A conduit extends across the plunger head between the proximal chamber and the opening at the distal end of the syringe barrel. A fluid is contained in the proximal chamber, thereby providing a pre-filled syringe assembly prepared for use for delivery of the fluid.

In still a further embodiment, a method of delivering a fluid involves providing: a syringe assembly comprising a syringe barrel having an inside surface defining a chamber, a proximal end, and a distal end having an opening therethrough; a plunger assembly comprising an elongate plunger rod and a plunger head disposed on the plunger rod and slidably disposed within the syringe barrel, the plunger head separating the chamber of the syringe barrel into a proximal chamber adjacent the proximal end and a distal chamber adjacent the distal end, wherein a fluid is contained in the proximal chamber; and a conduit extending the plunger assembly further comprising an actuator portion which at least partially extends externally outside of the syringe barrel between the proximal chamber and the opening at the distal end of the syringe barrel. The method further involves positioning a thumb on the syringe assembly at a position proximate to the proximal end of the syringe barrel, and at least one forefinger on the actuator portion, and applying a squeezing motion to move the at least one forefinger and the thumb toward each other. Such motion moves the actuator portion toward the proximal end of the syringe barrel and effects movement of the plunger head toward the proximal end of the syringe barrel to expel fluid contained in the proximal chamber through the conduit and out of the syringe barrel through the opening in the distal end.

BRIEF DESCRIPTION OF THE DRAWINGS

FIG. 1C is a side plan view of the syringe assembly of FIG. 1A.

FIG. 1D is a side cross-sectional view of the syringe assembly of FIG. 1A.

FIG. 1D-1 is an enlarged side cross-sectional view of the syringe assembly of FIG. 1A showing the details of the protrusions.

FIG. 8A is a perspective view of the syringe assembly of FIG. 7A shown after dispensing of the medication after use.

FIG. 8B is a front plan view of the syringe assembly of FIG. 8A after use.

DETAILED DESCRIPTION

Figure 1A:
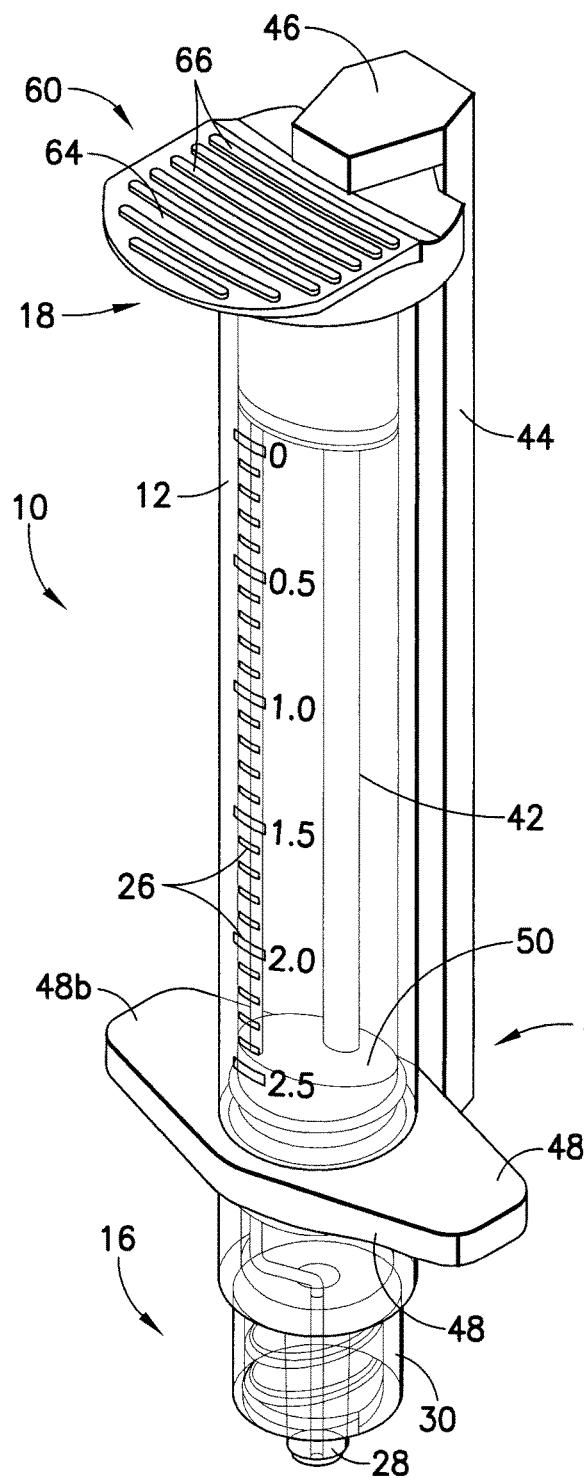
FIG. 1A is a perspective view of a syringe assembly in one embodiment of the present invention shown in a pre-filled state prior to use.
Figure 1B:
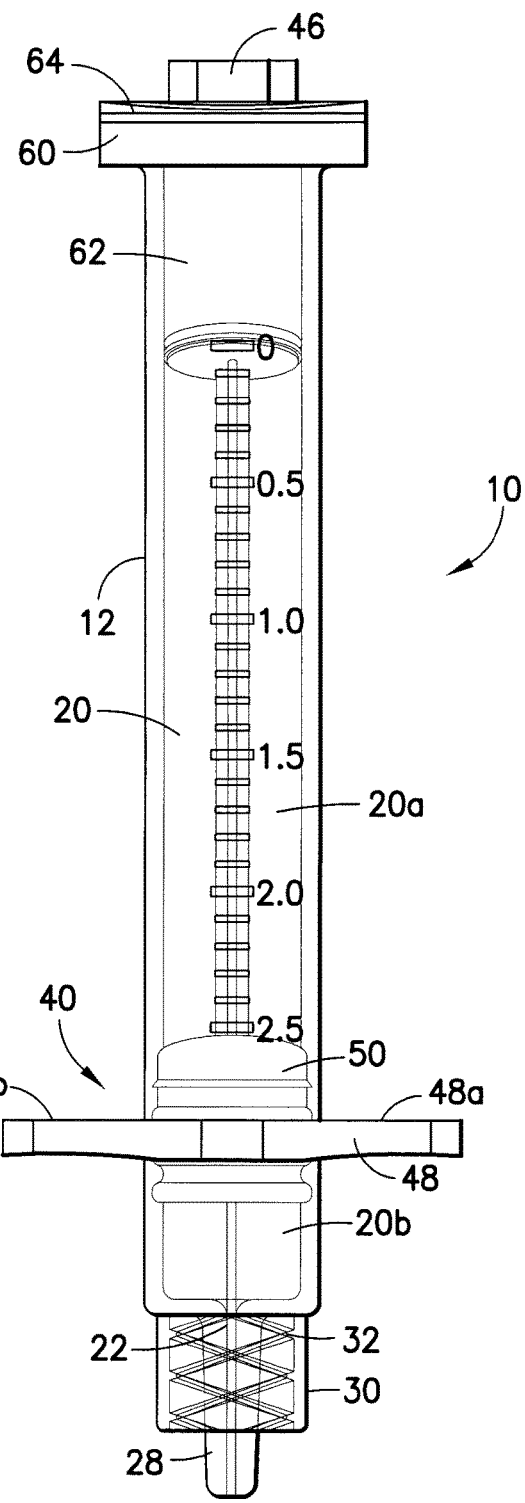
FIG. 1B is a front plan view of the syringe assembly of FIG. 1A.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1A-1D, which depict a syringe assembly, generally indicated as 10, adapted for dispensing and delivery of a fluid. Syringe assembly 10 is intended for use for injection or infusion of fluid such as a medication into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with an intravenous (IV) connection assembly.

Syringe assembly 10 includes syringe barrel 12 defined by barrel wall 14 extending between a forward or distal end 16 and a rearward or proximal end 18, thereby defining interior chamber 20 of syringe barrel 12. Syringe barrel 12 may be in the general form of an elongated cylindrical barrel as is known in the art for the general shape of a hypodermic syringe, although other forms for containing a fluid for delivery are also contemplated. Forward end 16 of syringe barrel 12 includes an outlet opening 22, and rearward end 18 is generally open-ended, but is intended to be closed off to the external environment, as will be discussed in more detail herein. Syringe barrel 12 may include markings, such as graduations 26 on the wall thereof, for providing an indication as to the level or amount of fluid contained within syringe barrel 12. Such markings may be provided on the external wall, the internal wall, or integrally formed or otherwise within the wall of syringe barrel 12. Alternatively or in addition thereto, the markings may provide a description of the contents of the syringe, or other identifying information, as may be known in the art.

As noted, forward end 16 of syringe barrel 12 includes an outlet opening 22. The profile of outlet opening 22 may be adapted for engagement with a separate device, such as a needle assembly or IV connection assembly, and therefore may include a mechanism for such engagement, for example, a generally tapered luer tip 28, for engagement with a separate tapered luer mating surface (not shown) of such a separate device for attachment therewith. In addition, a mechanism for locking engagement therebetween may also be provided, such as luer lock 30 including interior threads 32. Such luer connections and luer locking mechanisms are well known in the art. Additionally, syringe barrel 12 includes at least one opening through the wall thereof extending into the interior chamber 20 adjacent forward end 16, such as vent 34, the use of which will be described in further detail herein.

Syringe assembly 10 further includes a plunger assembly 40, a portion of which is disposed at least partially within syringe barrel 12. Plunger assembly 40 provides a mechanism for dispensing fluid contained within the interior chamber 20 of syringe barrel 12. In particular, plunger assembly 40 includes a plunger head or stopper portion 50 disposed within interior chamber 20, and in contact with the internal surface of syringe barrel wall 14, thereby separating interior chamber 20 into a proximal chamber 20a adjacent proximal or rearward end 18, and a distal chamber 20b adjacent distal or forward end 16 of syringe barrel 12. Plunger head 50 may include one or more annular ribs extending about the outside perimeter thereof, such as rib 52, for providing sealing engagement with the interior surface of syringe barrel wall 14.

Plunger head 50 is adapted for movement within the interior chamber 20 of syringe barrel 12, with plunger head 50 sliding or riding along the interior surface of syringe barrel wall 14. Such movement may be effected by a separate actuator portion of plunger assembly 40 which at least partially extends externally outside of syringe barrel 12. For example, an actuator in the form of a perimetrical flange collar 48 including finger flanges 48a and 48b may extend external to syringe barrel 12, for example, along the external surface of syringe barrel wall 14, and may be interconnected with plunger head 50, such as directly through an opening or channel through wall 14, through an assembly which extends through generally open-ended rearward end 18 of syringe barrel 12, or through a further interconnection. While the actuator is shown as a flange collar 48 including a pair of finger flanges 48a, 48b, it is contemplated that any number of finger flanges may be present.

In one embodiment as depicted in FIGS. 1A-1D, plunger assembly 40 includes a plunger rod 42 for connecting plunger head 50 with external flange collar 48 and finger flanges 48a and 48b. Plunger rod 42 and plunger head 50 may be integrally formed, or may be separate elements that are attached or otherwise interconnected together. For example, plunger rod 42 may be constructed of a stiff polymeric material, with plunger head 50 formed from a separate silicone or rubberized material that is molded integrally with plunger rod 42, such as through a two-shot molding process, or may be a separate material that is mechanically attached or adhesively fixed to plunger rod 42.

Various assemblies are contemplated for interconnecting actuator portion of plunger assembly 40 with plunger head 50 through open rearward end 18 of syringe barrel 12. For example, plunger rod 42 of plunger assembly 40 may include a first elongated portion that is connected with plunger head 50 and that extends within the interior 20 of syringe barrel 12 and out through open rearward end 18 of syringe barrel 12. As shown in FIG. 1D, plunger assembly 40 may further include an external arm 44 extending externally along syringe barrel 12 for connection with flange collar 48 and finger flanges 48a and 48b, and with connecting arm 46 interconnecting internal plunger rod 42 and external arm 44. In this manner, finger flanges 48a, 48b are interconnected with plunger head 50 through the open rearward end 18 of syringe barrel 12 by way of external arm 44, connecting arm 46, and internal plunger rod 42, respectively.

As noted, rearward end 18 of syringe barrel 12 is open-ended. Syringe assembly 10 may further be provided with a closure, such as cap 60, for closing the open rearward end 18 of syringe barrel 12, thereby providing interior chamber 20 as a closed chamber. Cap 60 includes an elongated portion in the form of neck 62 that has an outer diameter substantially the same as an inner diameter of syringe wall 14, so as to provide an interference fit therein, thereby holding cap 60 in place. Cap 60 may be fixedly adhered in place, such as through a mechanical engagement, a biocompatible adhesive, sonic welding, etc. Cap 60 includes a finger pad portion 64 that extends external to syringe barrel 12, which may be provided with finger ribs 66 for providing a tactile surface for a user. Cap 60 may also include an angled profile 68 on the end of neck 62 extending within syringe barrel 12, providing a recessed area adjacent proximal end 18 of syringe barrel 12 for accommodating the outflow of fluid, as will be described in more detail herein. Plunger head 50 may also include an angled profile 54 at a proximal end thereof for cooperating engagement with angled profile 68 of cap 60 upon full displacement of plunger head 50 within interior chamber 20, as will be described in further detail.

Syringe assembly 10 further includes a conduit 70 extending between a first end 72 positioned adjacent forward end 16 of syringe barrel 12, and a second end 74 positioned adjacent rearward end 18 of syringe barrel 12, with fluid channel 76 extending therethrough. Conduit 70 extends across plunger head 50, with first end 72 of conduit 70 extending within or through forward opening 22 of syringe barrel 12, providing for fluid communication with forward opening 22, and with second end 74 of conduit 70 extending within proximal chamber 20a, such that fluid channel 76 is in fluid communication with proximal chamber 20a. Second end 74 of conduit 70 may be positioned within the recess at proximal end 18 created by the angled profile 68 of cap 60. In this manner, the rearward-most or proximal-most portion of proximal chamber 20a is established by the recess of angled profile 68, with an inlet into conduit 70 provided at second end 74 being positioned in this proximal-most portion of proximal chamber 20a. This positioning is particularly useful for removing any air trapped within proximal chamber 20a prior to expelling any drug therefrom, as will be described in more detail with respect to the use of syringe assembly 10.

All of the components of syringe assembly 10 may be constructed of any known material, and are desirably constructed of medical grade polymers.

Syringe assembly 10 is particularly useful as a pre-filled syringe, and therefore may be provided for end use with a fluid, such as a medication, contained within proximal chamber 20a of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

In use, syringe assembly 10 is provided with a medication pre-filled and contained within proximal chamber 20a of syringe barrel 12. For use, syringe assembly 10 is grasped with the user's thumb on finger pad 64 and with the user's fingers extending between finger flanges 48a and 48b of flange collar 48. In this manner, syringe assembly 10 is grasped by the user in a well known and well recognized manner similar to the operation of a conventional hypodermic syringe.

Prior to dispensing of medication, any air trapped within proximal chamber 20a can be expelled by arranging syringe assembly 10 with the forward end 16 pointed downward, such that any air within proximal chamber 20a will be forced toward rearward end 18 at the recessed area established by the angled profile 68 of cap 60. With second end 74 of conduit 70 positioned within this recess adjacent angled profile 68, initial movement of plunger assembly 40, by sliding movement of plunger head 50, will cause any such air trapped within proximal chamber 20a at the recess of angled profile 68 to be expelled through second end 74, into conduit 70 and out first end 72 into outlet opening 22 out from syringe barrel 12 prior to any medication being expelled.

Figure 2:
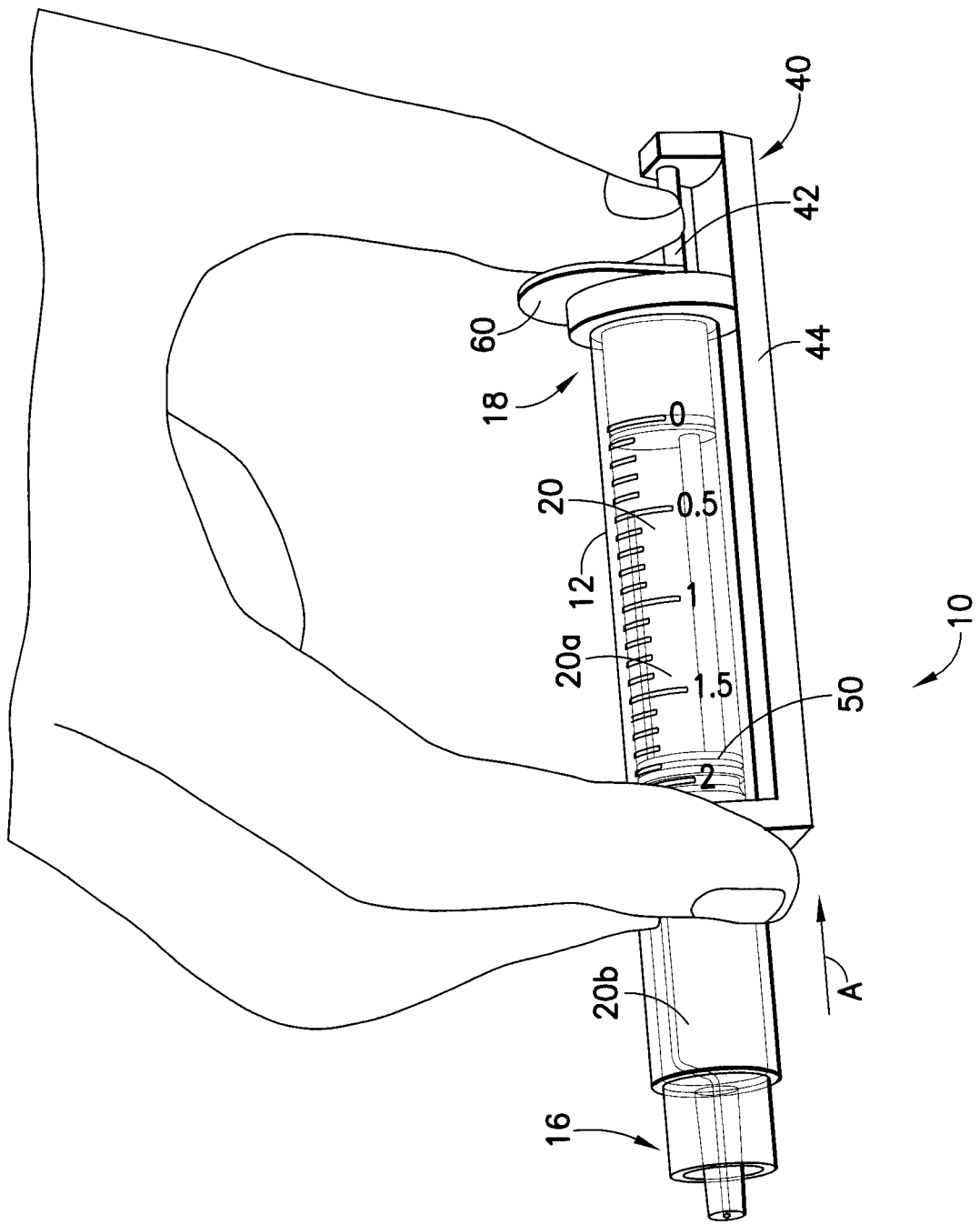
FIG. 2 is a perspective view of the syringe assembly of FIG. 1A shown during use by a user.
Figure 3:
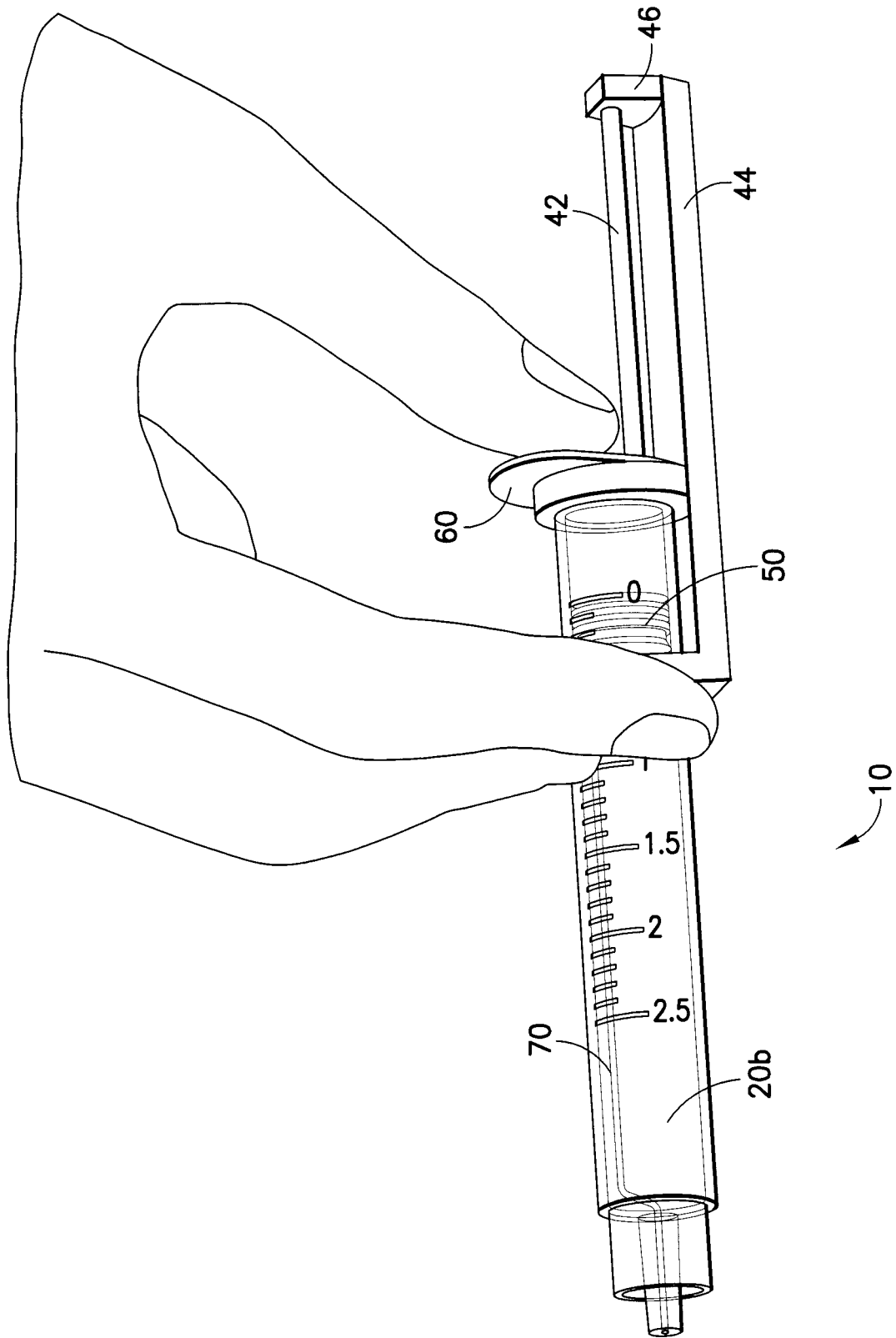
FIG. 3 is a perspective view of the syringe assembly of FIG. 1A shown after use by a user after the medication is expelled.
Figure 4A:
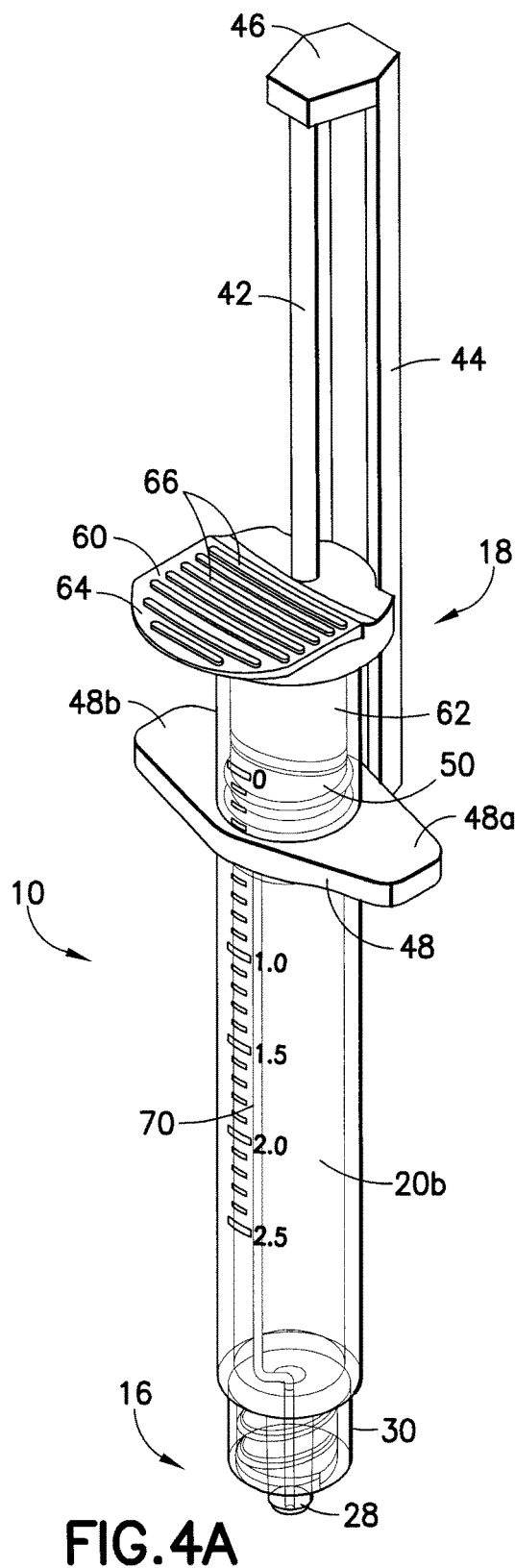
FIG. 4A is a perspective view of the syringe assembly of FIG. 1A shown after dispensing of the medication after use.
Figure 4B:
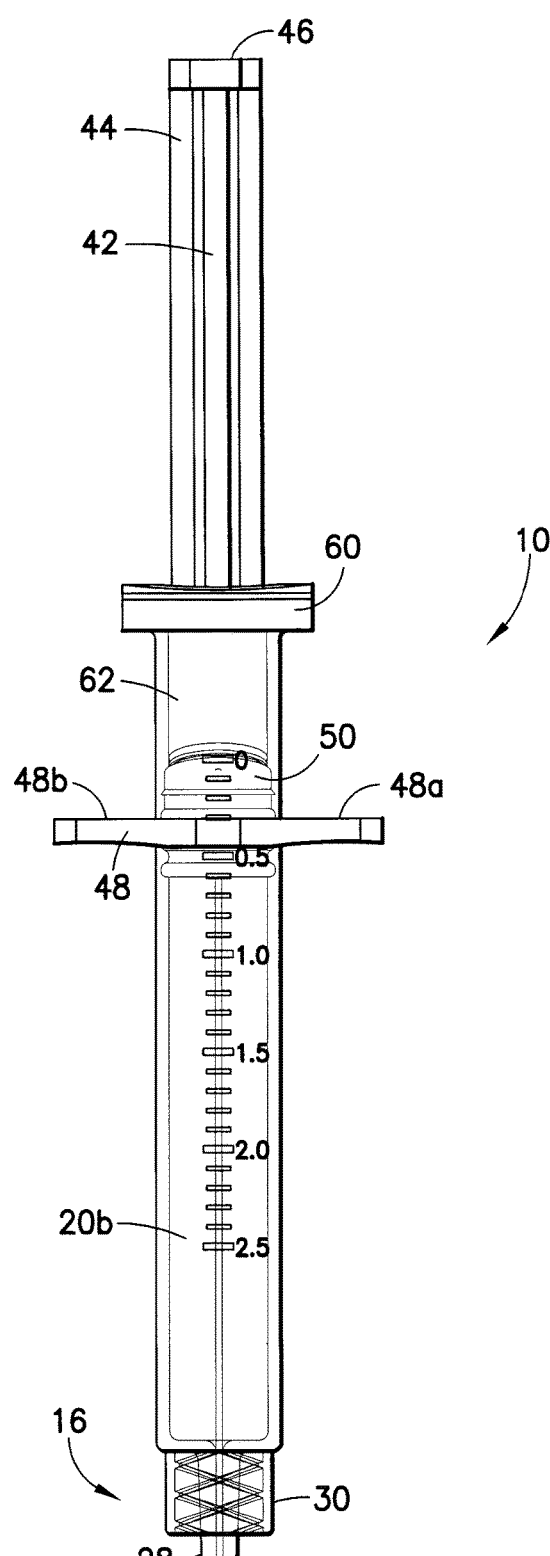
FIG. 4B is a front plan view of the syringe assembly of FIG. 4A after use.
Figure 4C:
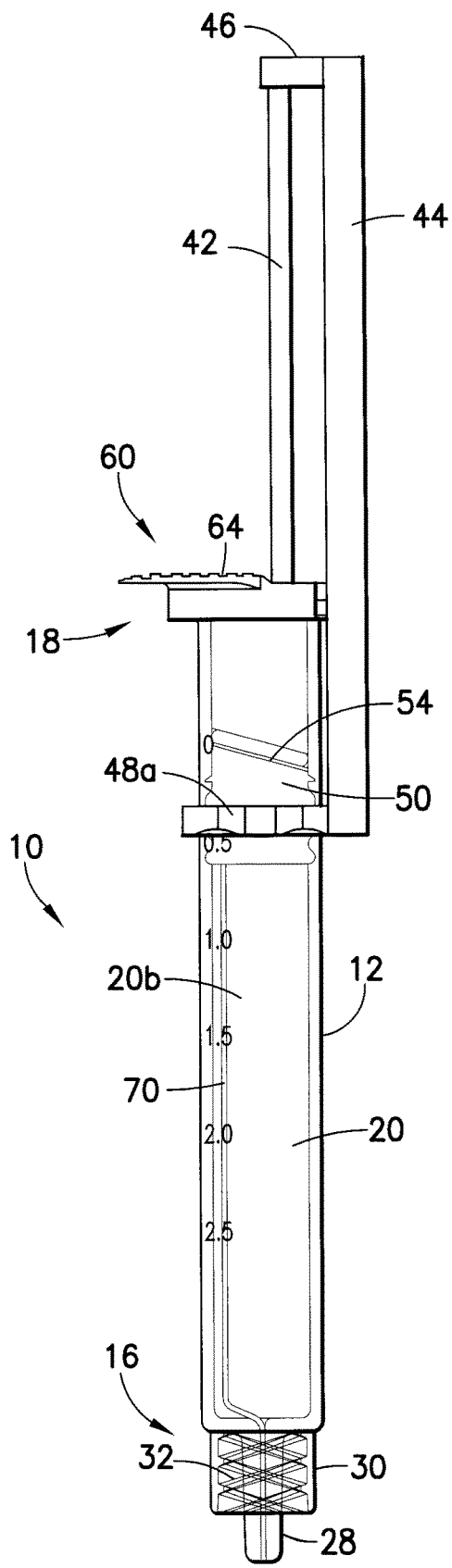
FIG. 4C is a side plan view of the syringe assembly of FIG. 4A after use.
Figure 4D:
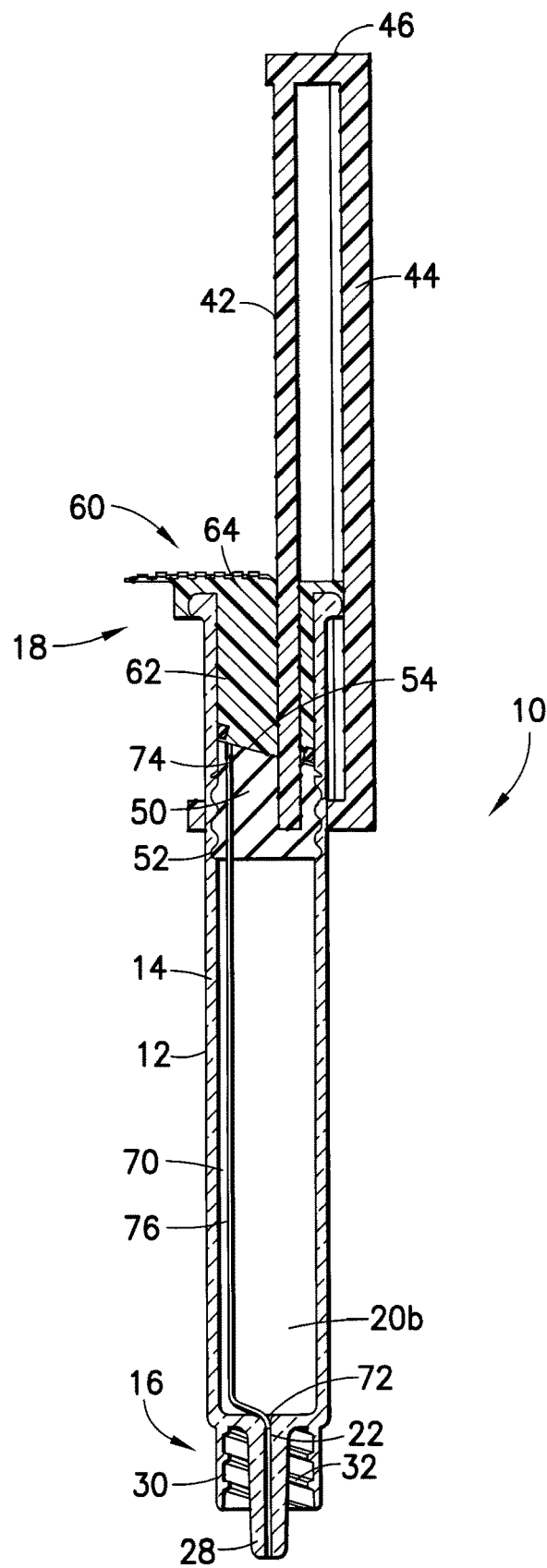
FIG. 4D is a side cross-sectional view of the syringe assembly of FIG. 4A after use.

The user can attach luer tip 28 to a separate needle assembly or IV connection assembly and lockingly engage through threads 32 of luer lock 30 in a known manner. When it is desired to deliver the medication, the user effects a squeezing movement between the thumb and forefingers as shown in FIG. 2, thereby causing finger flanges 48a, 48b and flange collar 48 to move in the direction of arrow A away from distal or forward end 16 and toward proximal or rearward end 18. Such movement of finger flanges 48a, 48b and flange collar 48 is transferred to plunger head 50 through the interconnection of internal plunger rod 42, external arm 44, and connecting arm 46 that interconnects plunger head 50 with flange collar 48. Such movement of plunger head 50 within interior chamber 20 of syringe barrel 12 reduces the volume of proximal chamber 20a, thereby creating a positive pressure therein. In order to prevent a negative pressure within distal chamber 20b, air can be drawn into distal chamber 20b through vent 34, which provides a mechanism for air flow between distal chamber 20b and the external environment.

Since proximal chamber 20a is sealed to the external environment through plunger head 50 and through cap 60 at a rearward opening 24, the medication fluid within proximal chamber 20a is forced into fluid channel 76 at second end 74 of fluid conduit 70. Such fluid medication travels through fluid channel 76 and out through first end 72 of conduit 70, entering into forward opening 22. In this manner, the fluid medication can be expelled from the syringe barrel 12 through forward opening 22, and into the separate needle assembly or IV assembly and into the patient.

Upon full movement of plunger head 50 through syringe barrel 12, plunger head 50 "bottoms out", with plunger head 50 contacting the internal end of cap 60, as shown in FIGS. 3 and 4A-4D, with the corresponding angled profiles 54, 68 of plunger head 50 and cap 60, respectively, in corresponding engagement. The second end of conduit 74 is arranged within proximal chamber 20a at a position adjacent the portion of the angled profile 68 of cap 60 that is closest to proximal or rearward end 18. In this manner, the fluid medication is funneled toward first end 72 of conduit 70, and the internal volume of proximal chamber 20a remains filled with fluid medication through the entire sliding movement of plunger head 50 through syringe barrel 12. At this point, plunger rod 42, external arm 44, and connecting arm 46 all extend substantially externally of syringe barrel 12.

Figure 13:
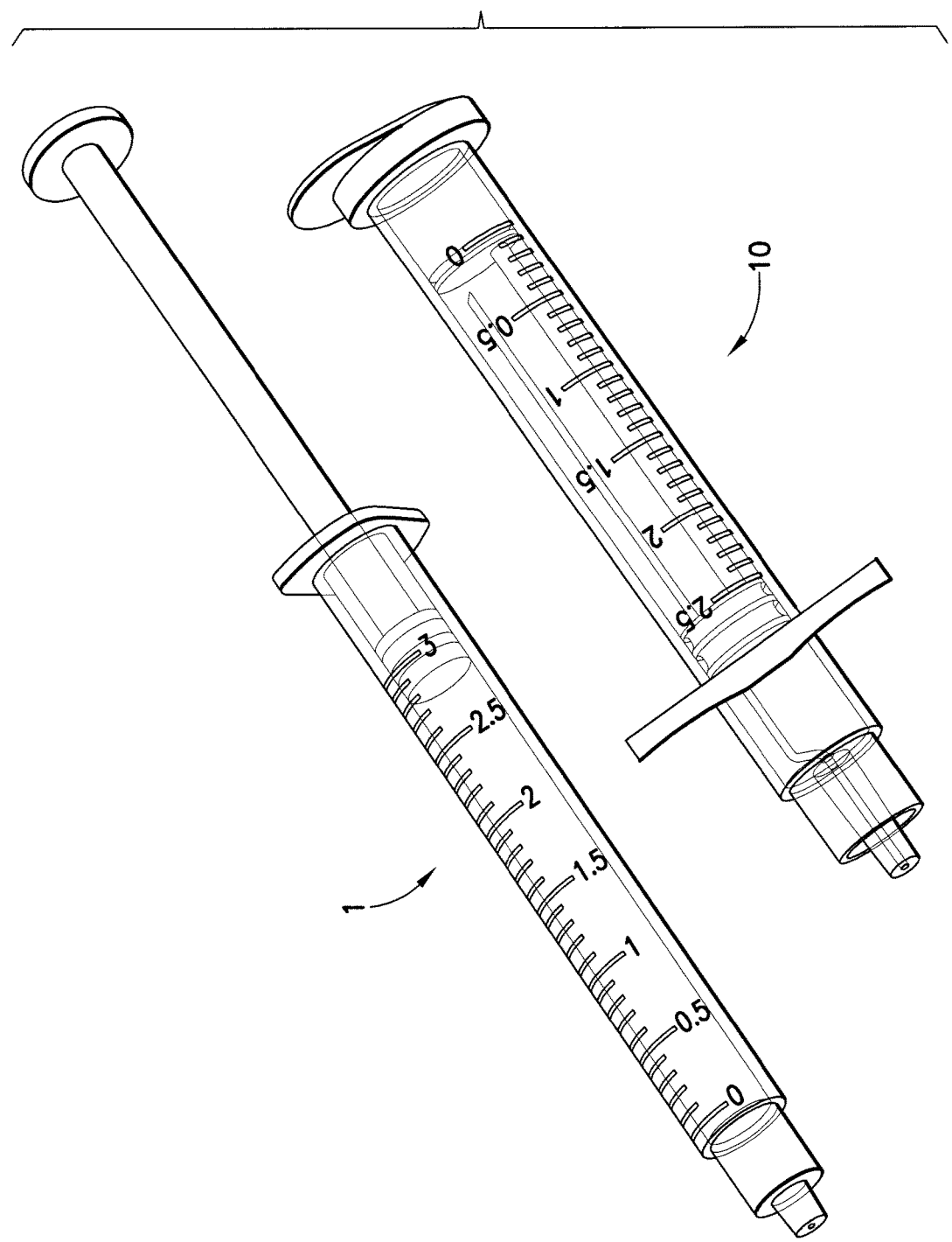
FIG. 13 is a perspective view comparing a conventional syringe to a syringe assembly in accordance with the present invention.

With such an arrangement, the overall size and shape of syringe assembly 10 when filled for use is of an overall profile similar to a conventional syringe after use, with a plunger completely extended within a syringe barrel, as seen in FIG. 13, which depicts the profile of a conventional syringe 1 in comparison to syringe assembly 10 in accordance with an embodiment of the present invention. As such, the profile is significantly reduced from that of a conventional pre-filled syringe, which includes the plunger retracted from the barrel prior to use.

Figure 5A:
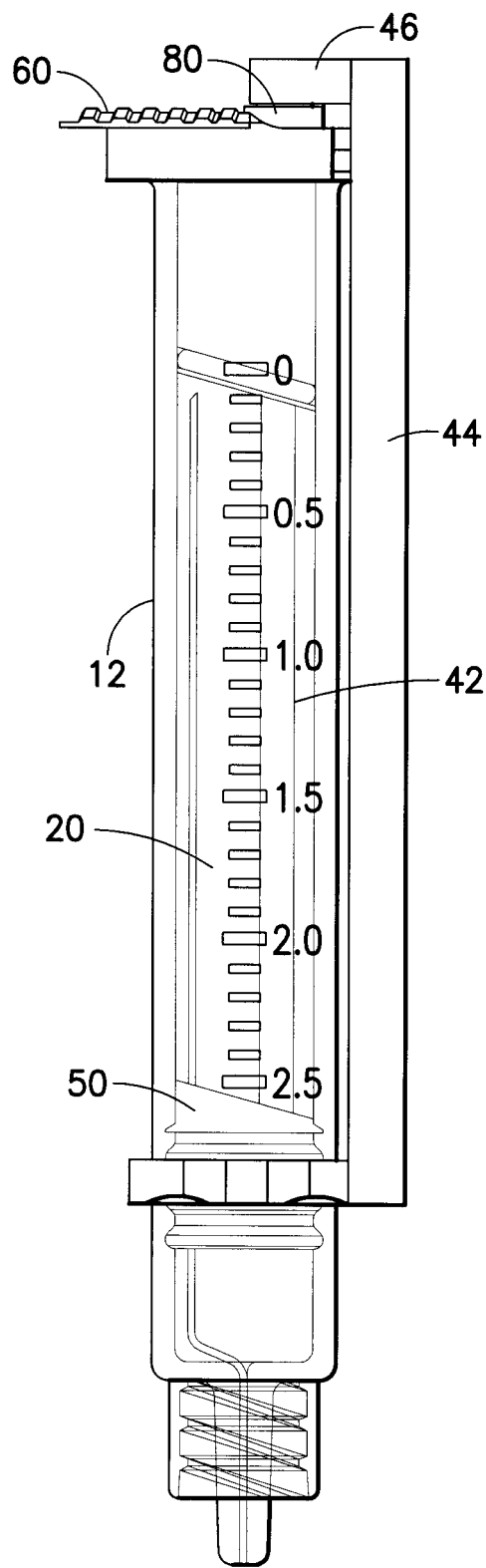
FIG. 5A is a side plan view of a syringe assembly similar to that of FIG. 1A shown in a pre-filled state prior to use and further including a bellows.
Figure 5B:
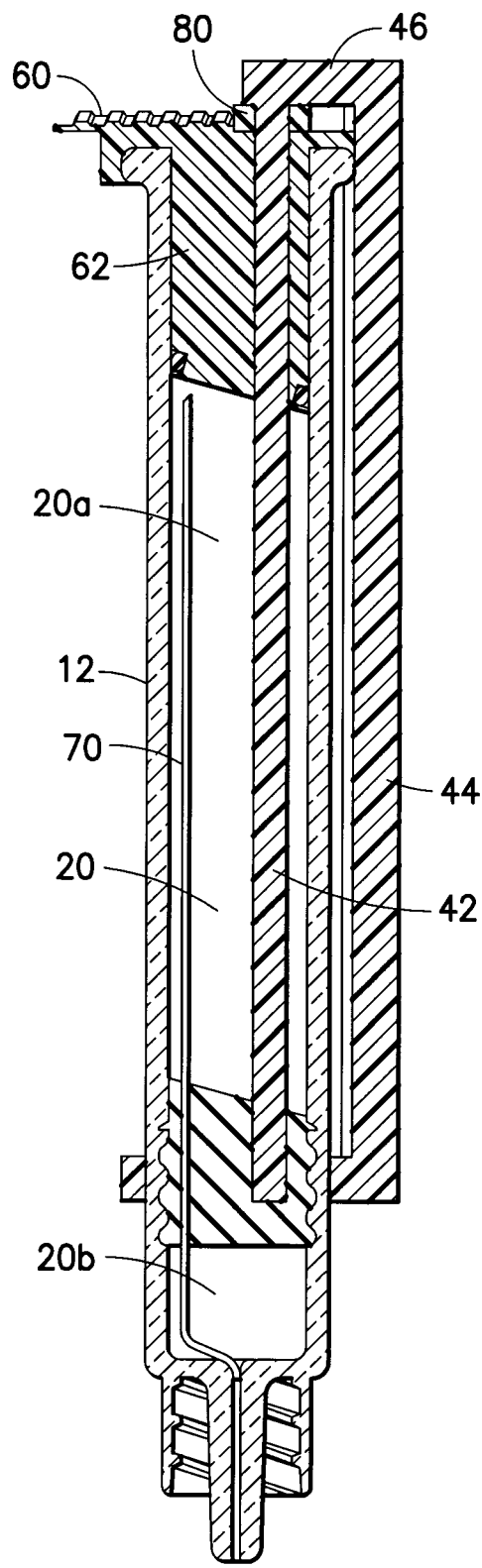
FIG. 5B is a side cross-sectional view of the syringe assembly of FIG. 5A.
Figure 5C:
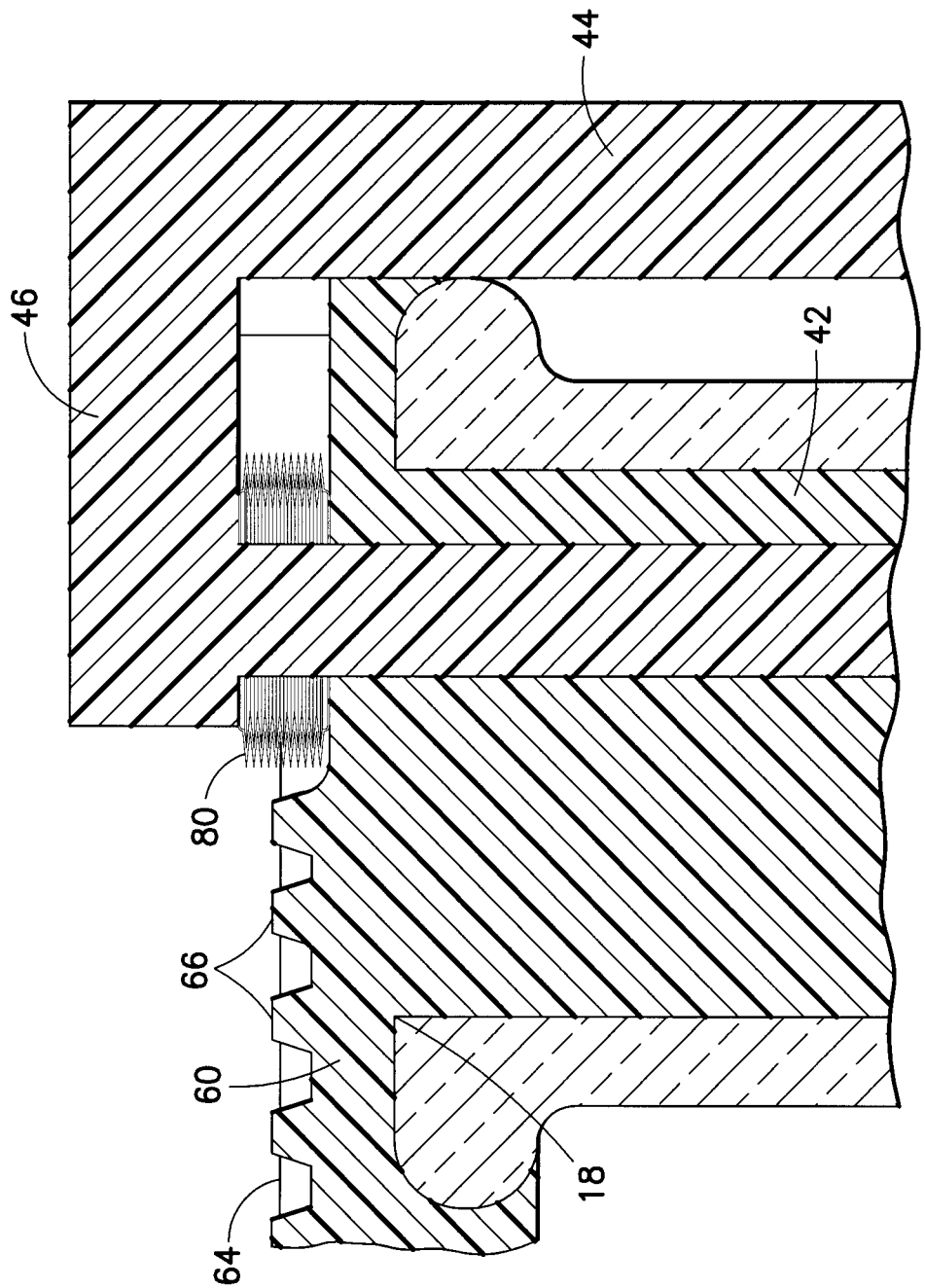
FIG. 5C is an enlarged side cross-sectional view of FIG. 5A showing the details of the bellows.
Figure 6A:
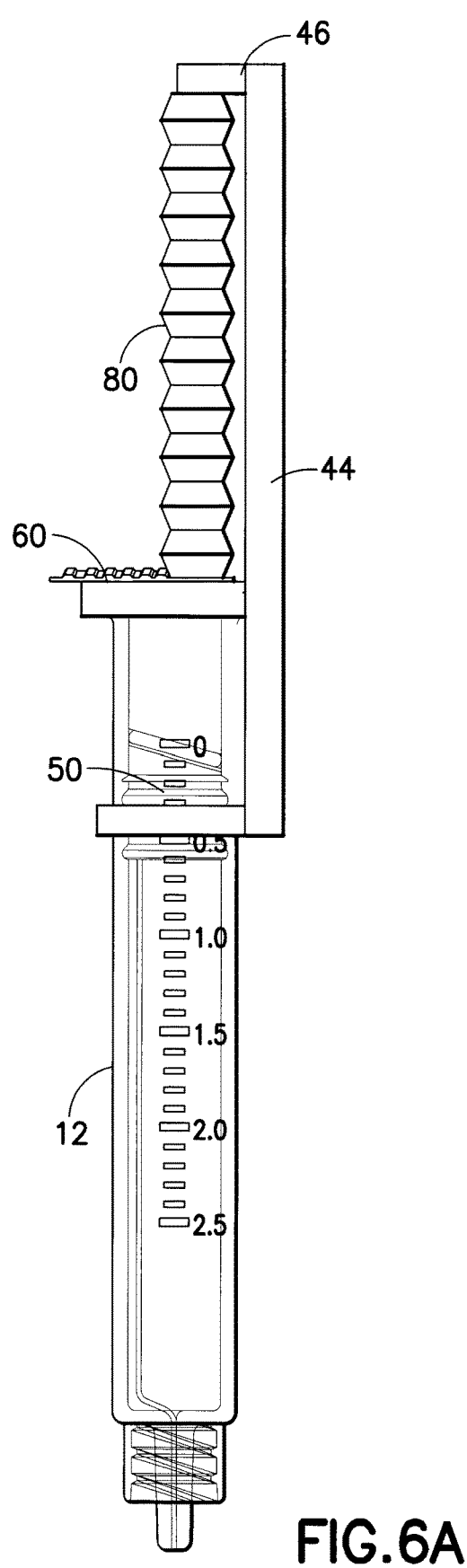
FIG. 6A is a side plan view of the syringe assembly of FIG. 5A shown after dispensing the medication after use with the bellows expanded.
Figure 6B:
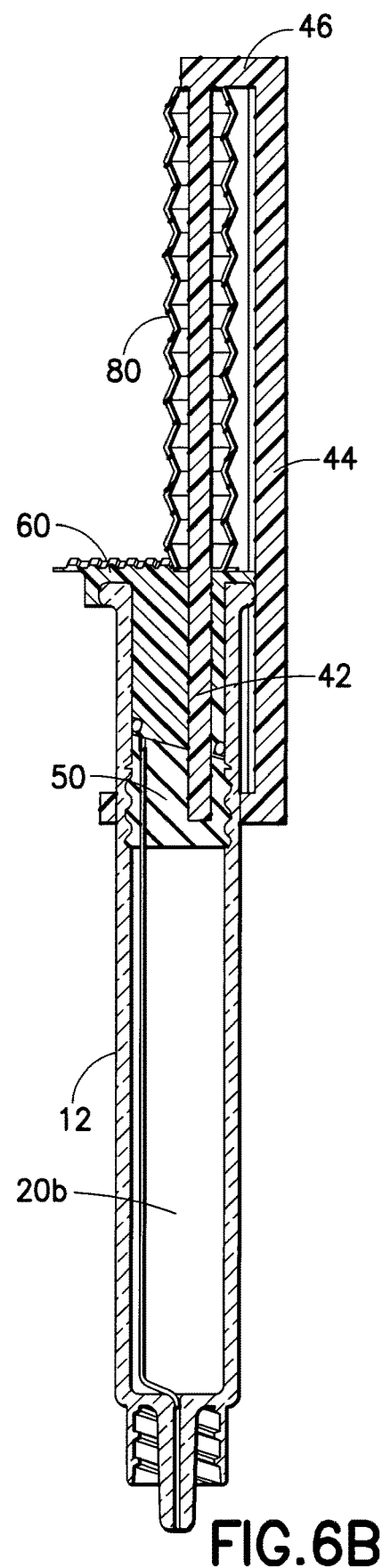
FIG. 6B is a side cross-sectional view of the syringe assembly of FIG. 6A.
Figure 6C:
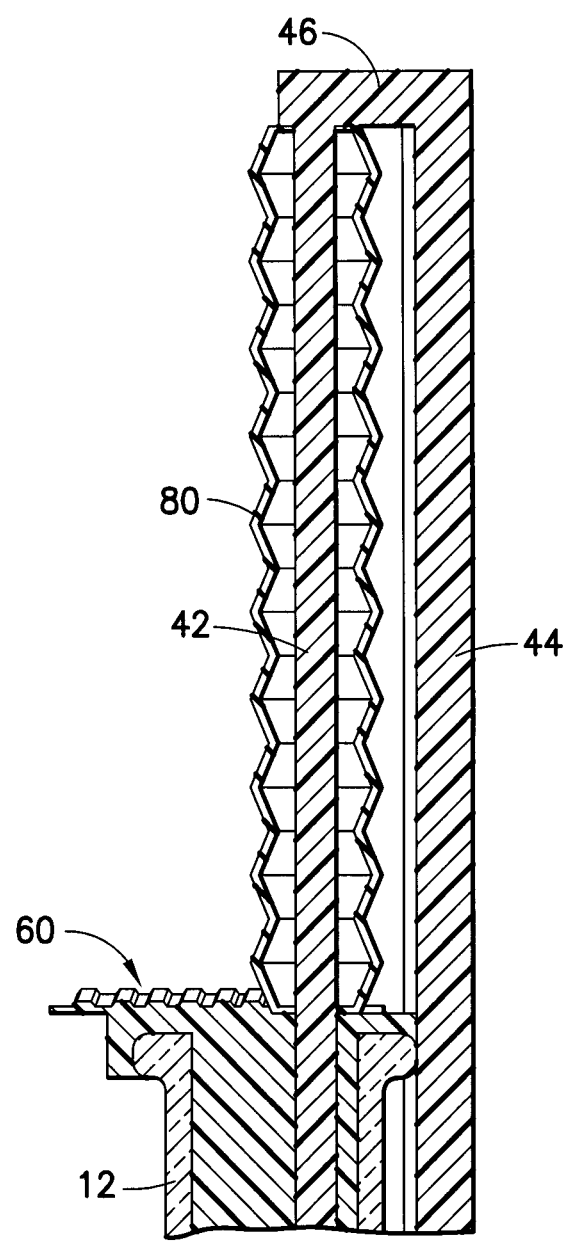
FIG. 6C is an enlarged side cross-sectional view of FIG. 6A showing the details of the expanded bellows.
Figure 7A:
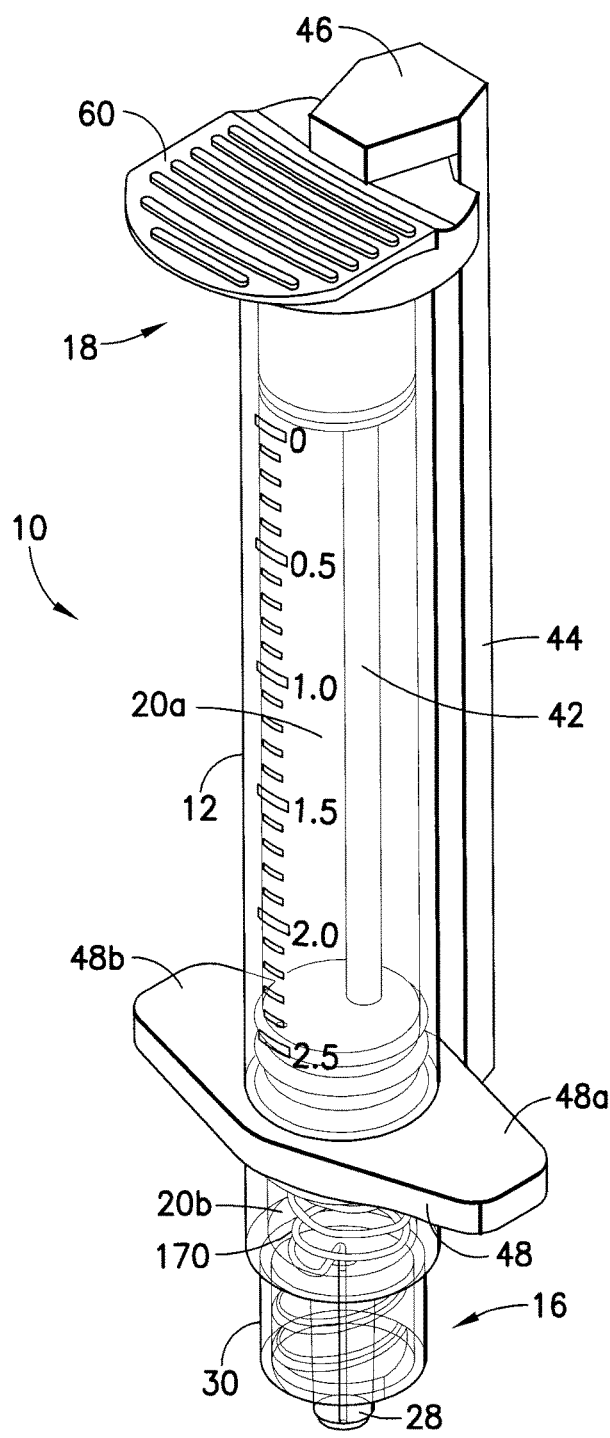
FIG. 7A is a perspective view of a syringe assembly in a further embodiment shown in a pre-filled state prior to use.
Figure 7B:
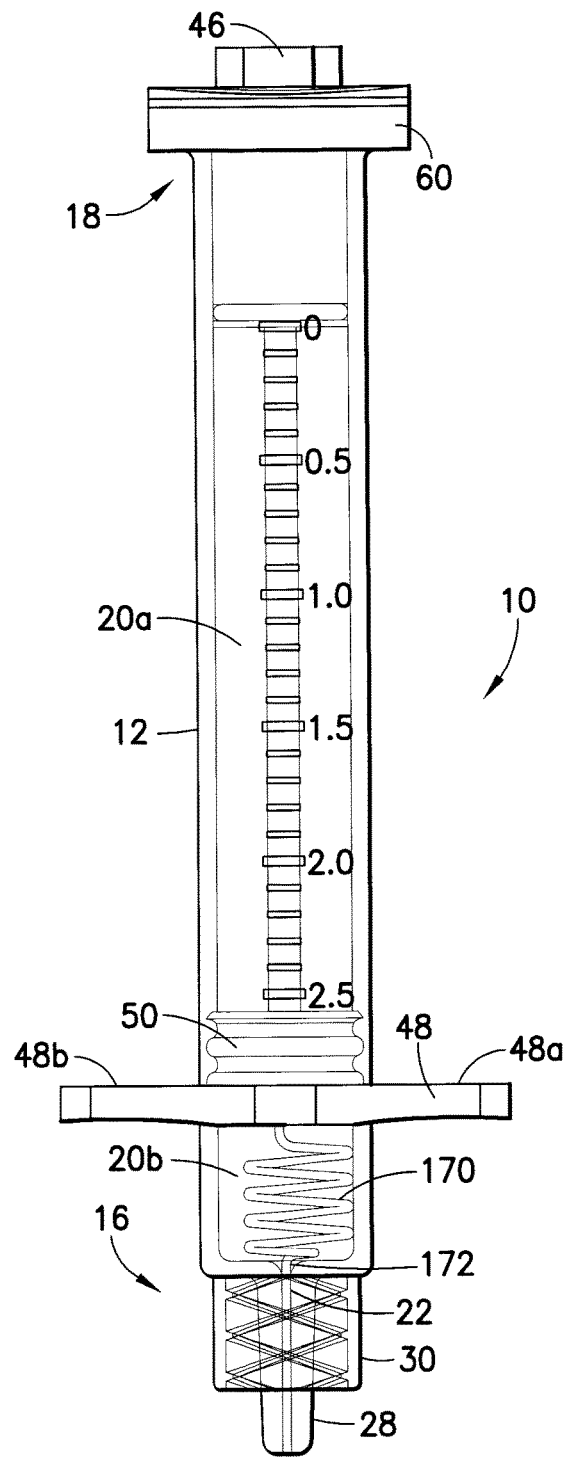
FIG. 7B is a front plan view of the syringe assembly of FIG. 7A.
Figure 7C:
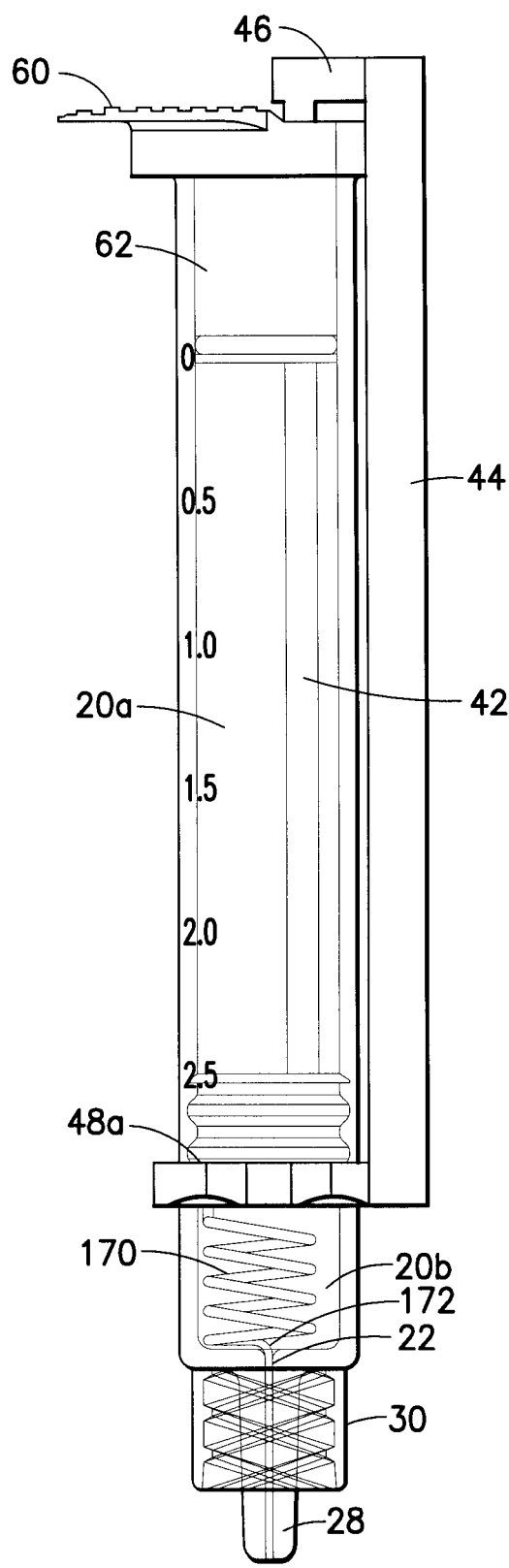
FIG. 7C is a side plan view of the syringe assembly of FIG. 7A.
Figure 7D:
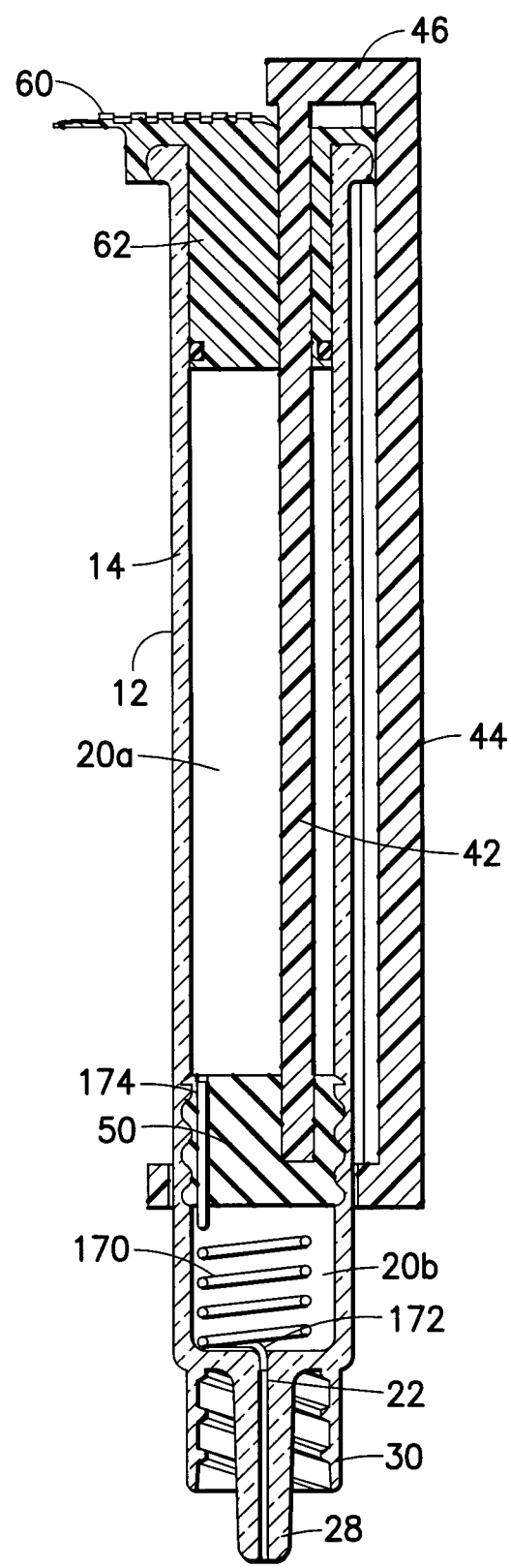
FIG. 7D is a side cross-sectional view of the syringe assembly of FIG. 7A.
Figure 8C:
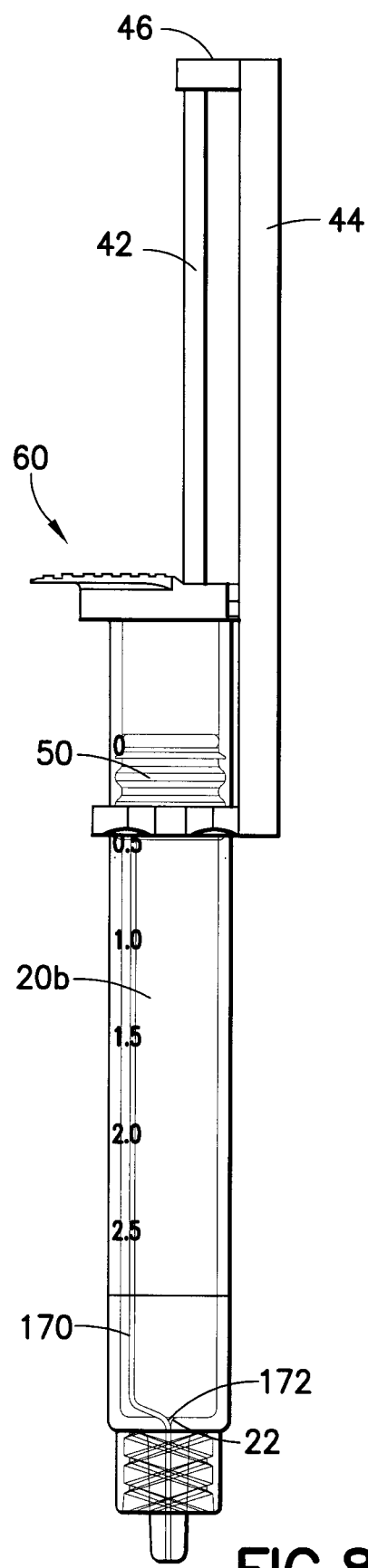
FIG. 8C is a side plan view of the syringe assembly of FIG. 8A after use.
Figure 8D:
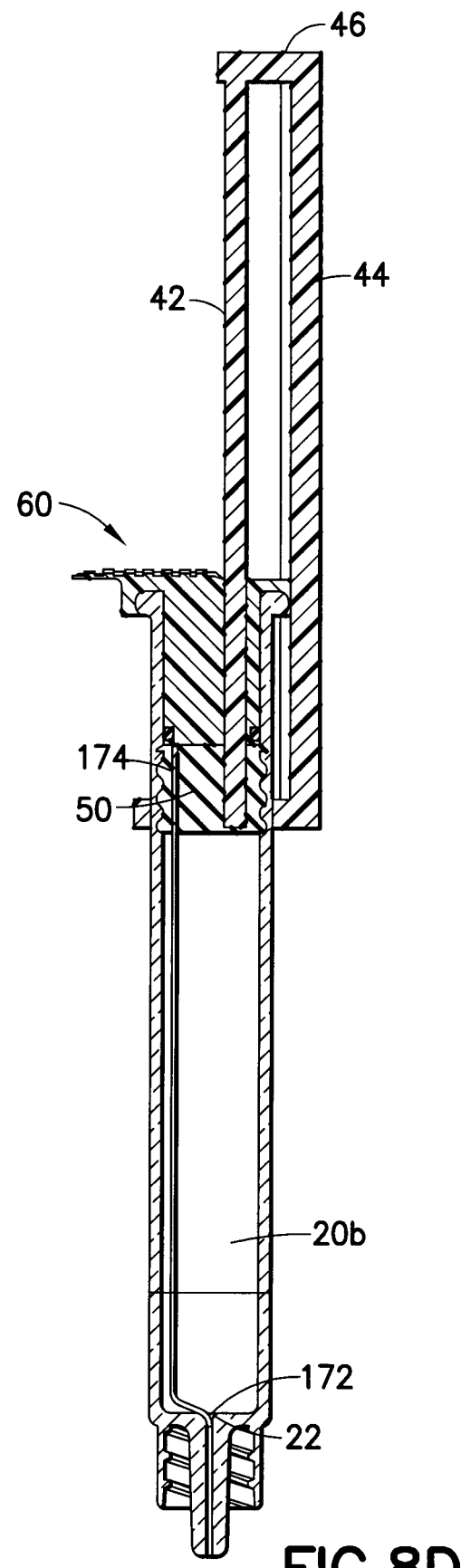
FIG. 8D is a side cross-sectional view of the syringe assembly of FIG. 8A after use.

FIGS. 5A-5C and 6A-6C depict syringe assembly 10 in an alternate embodiment that is substantially the same as that described above with respect to FIGS. 1A-4D, but further including a mechanism for preventing exposure to the syringe contents and for preventing contamination. In particular, during the injection and syringe discharge sequence as described above, the plunger rod 42 is retracted from within the syringe barrel 12. Prior to such retraction, the plunger rod 42 is in direct contact with the fluid contained within the proximal chamber 20a of syringe barrel 12. In order to prevent the user from being exposed to the contents of the syringe during the retraction of the plunger rod 42 based on the plunger rod 42 being "wetted" with such fluid, a barrier, such as an expandable bellows 80, can be provided. Bellows 80 can encompass the portion of plunger rod 42 that extends external to syringe barrel 12 during retraction. As such, bellows 80 encompasses and wraps around the externally exposed portion of plunger rod 42, and is adapted to expand upon retraction of plunger rod 42. For example, bellows 80 may be of an accordion-style construction, interconnected between an end of plunger rod 42 adjacent connecting arm 46 and extending to cap 60 at a location where plunger rod 42 extends through cap 60. When syringe assembly 10 is in a pre-filled state prior to use with plunger rod 42 extending within syringe barrel 12, bellows 80 is at least partially, and likely fully, collapsed, as shown in FIGS. 5A-5C. When plunger rod 42 is retracted to the exterior upon movement of finger flanges 48a, 48b, bellows 80 expands to encompass and maintain plunger rod 42 in a sealed environment. As such, any fluid in contact with plunger rod 42 is maintained within bellows 80 and is prevented from contacting the user. Moreover, if the user pushes the plunger rod 42 back into syringe barrel 12 during or after use, sterility is maintained within the syringe barrel 12, since bellows 80 prevents plunger rod 42 from contacting the external environment.

FIGS. 7A-7D and 8A-8D depict a syringe assembly in a further embodiment similar to that described above in the embodiments of FIGS. 1A-4C, but with a different arrangement for the conduit. In particular, in the embodiment of FIGS. 7A-7D and 8A-8D, conduit 170 is provided as an expandable or extendable member adapted for movement with plunger head 50. Conduit 170 is similar to conduit 70 described above, including an internal fluid channel extending between a first end 172 and a second end 174, and across plunger head 50, with first end 172 positioned adjacent forward end 16 of syringe barrel 12. In this embodiment, however, the second end 174 of conduit 170 extends across plunger head 50 and into proximal chamber 20a at a position directly adjacent the rearward or proximal end of plunger head 50, with second end 174 fixed with plunger head 50. As such, the fluid channel extending through conduit 170 is in fluid communication with proximal chamber 20a directly at the area of contact between plunger head 50 and proximal chamber 20a when syringe assembly 10 is in a pre-filled state prior to use, as opposed to extending entirely through syringe barrel 12 to rearward end 18 prior to use as in the prior embodiments. Furthermore, in the embodiment of FIGS. 7A-7D and 8A-8D, conduit 170 is extendable, such that when plunger head 50 slides or moves along syringe wall 14 within syringe barrel 12, the second end 174 of conduit 170 moves with plunger head 50. This may be accomplished, for example, by providing conduit 170 as a flexible tubing that can be contained within distal chamber 20b prior to use of syringe assembly 10 and extended during use, or as a wound coil that can be extended during use, or other manner.

Operation of syringe assembly 10 depicted in the embodiment of FIGS. 7A-7D and 8A-8D is similar to that of the prior described embodiments. It is noted, however, that in the embodiment of FIGS. 7A-7D and 8A-8D, syringe assembly 10 does not have to be arranged with the forward end 16 pointed downward in order to first expel any trapped air from within the syringe, but instead can be arranged with the forward end 16 pointed upward, as in a more conventional syringe operation, since the initial point of fluid flow out of proximal chamber 20a occurs directly at the interface of plunger head 50 within proximal chamber 20a in this embodiment. To expel medication, plunger assembly 40 is actuated as in the prior embodiment, upon movement of flange collar 48 through finger flanges 48a, 48b to cause movement of plunger assembly 40, thus causing fluid to flow from within proximal chamber 20a into the fluid channel of conduit 170 directly at second end 174 and out first end 172.

Figure 9:
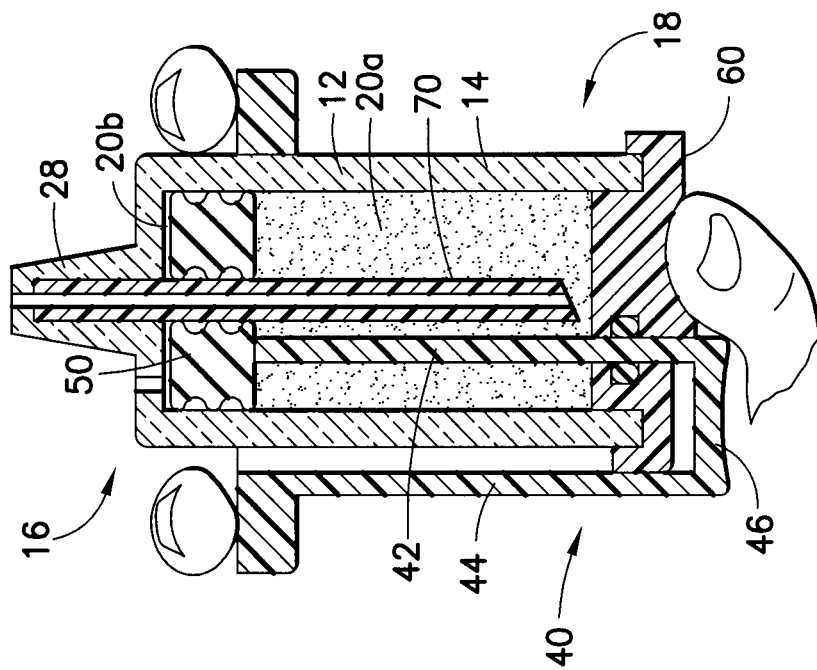
FIG. 9 is a side cross-sectional view of a syringe assembly in a further embodiment shown in a pre-filled state prior to use.
Figure 10:
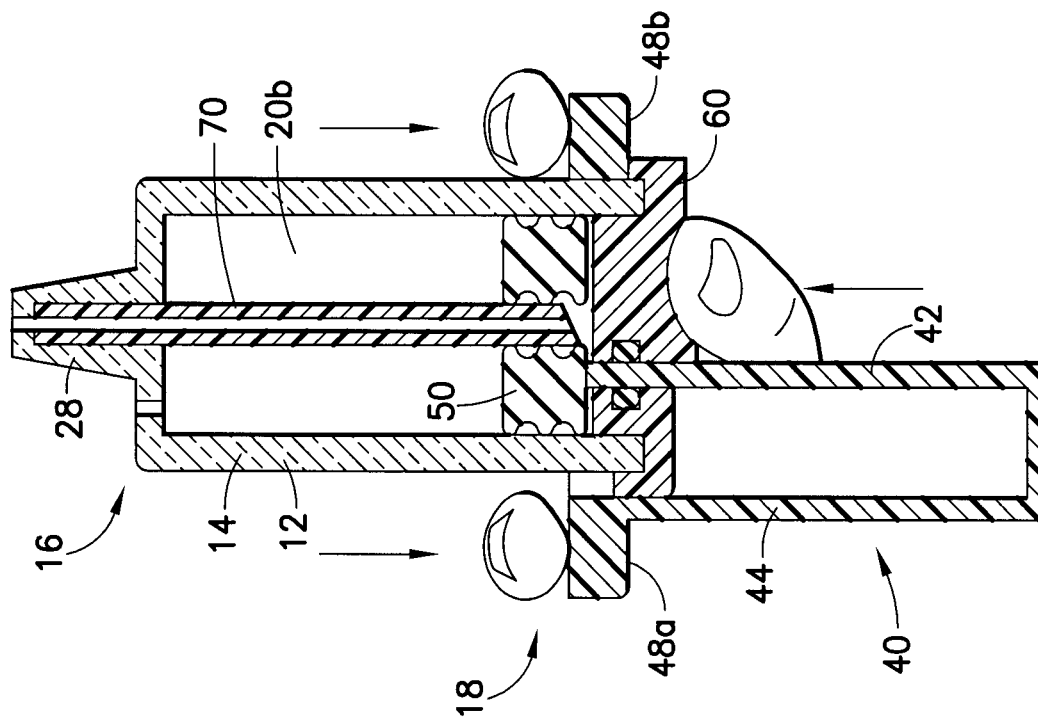
FIG. 10 is a side cross-sectional view of the syringe assembly of FIG. 9 shown after dispensing of the medication after use.

FIGS. 9 and 10 depict yet a further embodiment of a syringe assembly in accordance with the present invention. Syringe assembly 10 of FIGS. 9-10 includes similar components as that of the previously described embodiments of FIGS. 1A-4D, but with conduit 70 extending radially centered with respect to the general elongated axis of syringe assembly 10.

In a further embodiment, it is contemplated that a controlled dosing system could be provided. For example, an external surface of the syringe barrel 12 may be provided with notches or protrusions 58 along the graduations of the syringe barrel 12 at predetermined increments, such as at each 1 ml increment. A further protrusion or flap 56 would also be provided on the flange collar 48, such as a flap 56 extending around at least a portion of the internal perimeter of flange collar 48. As flange collar 48 rides along the outer surface of syringe barrel 12 toward the rearward end 18 during delivery of the medication, the flap 56 on the flange collar 48 would contact and interfere with each successive notch or protrusion 58 on the syringe barrel 12 (as shown in FIG. 1D-1), thereby providing an audible or tactile indication to the user of each predetermined dosage increment. In this manner, the user could hear or feel when each volume of dosage is delivered in specific increments.

Figure 12:
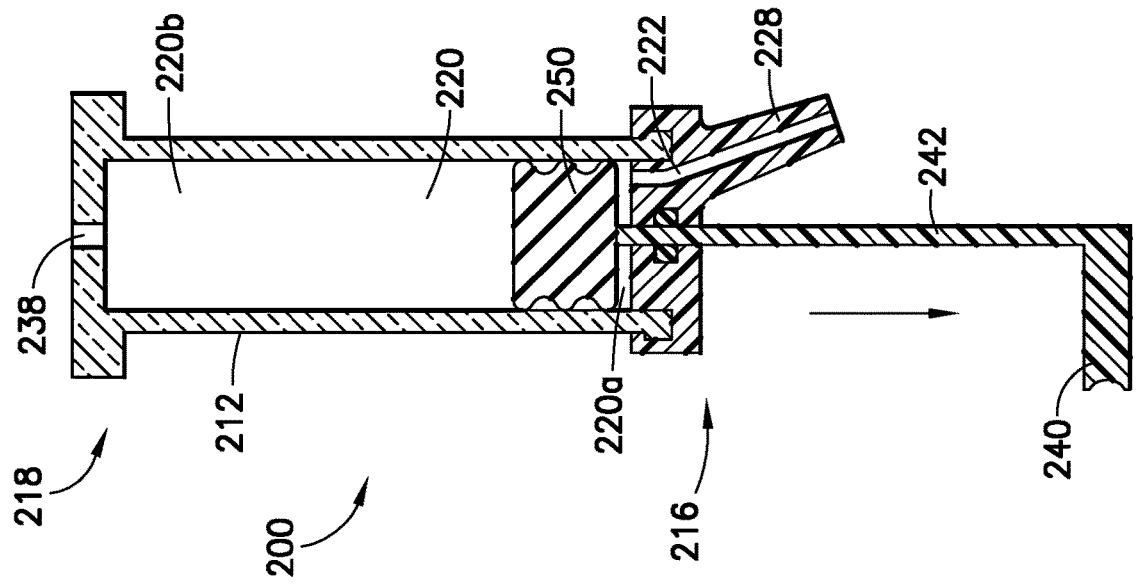
FIG. 12 is a side cross-sectional view of the syringe assembly of FIG. 11 shown after dispensing of the medication after use.
Figure 11:
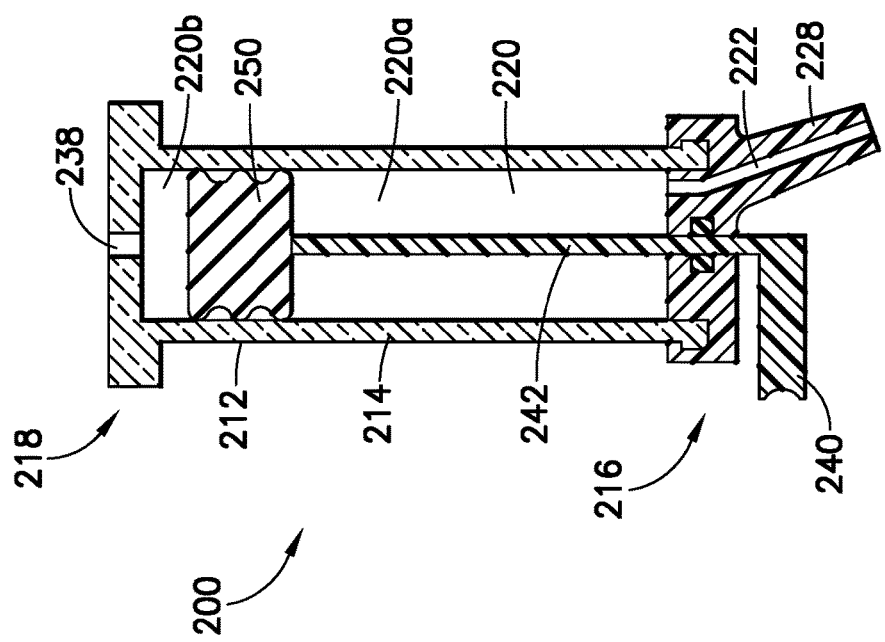
FIG. 11 is a side cross-sectional view of a syringe assembly in yet a further embodiment shown in a pre-filled state prior to use.

FIGS. 11 and 12 depict an alternate embodiment of a syringe assembly in accordance with the present invention. This alternate embodiment depicted in FIGS. 11 and 12 repositions the outlet end of the syringe assembly at the retraction end of the plunger rod. More particularly, syringe assembly 200 includes a syringe barrel 212 having a wall 214 extending between first end 216 and second end 218, forming an interior chamber 220 therein. First end 216 includes an opening 222, including a luer tip 228, which may be offset from the central axis of syringe assembly 200. Vent 238 is positioned adjacent second end 218.

Syringe assembly 200 further includes plunger assembly 240 including plunger rod 242 connected with plunger head 250. Plunger head 250 separates interior 220 of syringe barrel 212 into two distinct chambers, namely, first chamber 220a and second chamber 220b. Plunger rod 242 extends within interior 220 of syringe barrel 212 and out to the external environment through first end 216.

With such an arrangement, syringe assembly 200 works as follows. Fluid such as medication is contained within first chamber 220a of syringe barrel 212. To expel the medication, plunger assembly 240 is activated by pulling on plunger rod 242, thereby causing plunger head 250 to slide within syringe barrel 212. Medication is forced out through opening 222 at first end 216 of syringe barrel 212, which is in fluid communication with first chamber 220a. Vent 238 prevents negative pressure within second chamber 220b. In this manner, medication can be expelled and delivered through luer tip 228. Such an embodiment is similar to the prior discussed embodiments, albeit with the syringe opening 222 arranged in an opposite end of the assembly.

In each of the embodiments provided herein, the overall profile and dimensions of a syringe assembly when filled with a fluid such as medication prior to use is significantly reduced when compared with a traditional syringe. This reduced profile is accomplished by maintaining a significant portion of the plunger rod that is used for extending the stopper or plunger head within the syringe barrel when the syringe assembly is filled for use. Thus, the plunger rod occupies little space prior to use, thereby reducing packaging and eliminating waste. For disposal, the clinician has the option to push the plunger rod to its starting position to reduce the overall profile for disposal, such as in a sharps disposal container, thereby reducing the amount of storage space required for disposal.

In addition, certain embodiments involve a conventional operation for use of the syringe assembly to expel medication. For example, the tactile surfaces of the syringe assembly of the present invention include finger flanges and thumb presses situated for accommodating a user's fingers and thumb in a similar manner as with conventional syringes, such that a conventional squeezing movement expels the medication, albeit with a different arrangement within the syringe assembly causing an inverse movement of the fluids therein. As such, the user perceives no change in operation or use to dispense the medication even with the decreased overall profile of the assembly.

What is claimed is:

1. A syringe assembly having a reduced profile prior to use, comprising:
    a syringe barrel having an inside surface defining a chamber, a first end, and a second end;
    an opening located at the first end, the opening being offset from a central axis of the syringe assembly;
    a vent located adjacent the second end; and
    a plunger assembly comprising a plunger head slidably disposed within the syringe barrel and a plunger rod associated with the plunger head, the plunger head separating the chamber of the syringe barrel into a first chamber adjacent the first end and a second chamber adjacent the second end, wherein the plunger assembly includes an actuator portion at least partially extending outside the first end of the syringe barrel, and
    wherein a pulling movement on the plunger rod causes movement of the plunger head toward the first end of the syringe barrel causing contents of the syringe assembly to be expelled through the opening located at the first end.

2. The syringe assembly of claim 1, wherein the opening is associated with a luer tip.

3. The syringe assembly of claim 1, wherein the vent is configured to prevent negative pressure within the second chamber.

4. A method of delivering a fluid, comprising:
    providing a syringe assembly having a reduced profile prior to use comprising:
        a syringe barrel having an inside surface defining a chamber, a first end, and a second end;
        an opening located at the first end, the opening being offset from a central axis of the syringe assembly;
        a vent located adjacent the second end; and
        a plunger assembly comprising a plunger head slidably disposed within the syringe barrel and a plunger rod associated with the plunger head, the plunger head separating the chamber of the syringe barrel into a first chamber adjacent the first end and a second chamber adjacent the second end;
    providing an actuator portion at least partially extending outside the first end of the syringe barrel, said actuator portion being associated with the plunger rod; and
    applying a pulling force to the actuator portion to cause the plunger rod and the plunger head to move within the syringe barrel toward the first end of the syringe barrel causing the fluid to be expelled through the opening located at the first end.

\* \* \* \* \*